US012576272B2

(12) United States Patent
Bikson et al.

(10) Patent No.: US 12,576,272 B2
(45) Date of Patent: Mar. 17, 2026

(54) ENGAGEMENT COMPONENT SELECTION FOR CONTROL OF BIO-PSYCHIATRIC THERAPEUTIC TRAJECTORY (BTT)

(71) Applicant: The City University of New York, New York, NY (US)

(72) Inventors: Marom Bikson, Brooklyn, NY (US); Nigel Gebodh, New York, NY (US); Lucas Parra, Brooklyn, NY (US); Niranjan Khadka, Woodside, NY (US); Abhishek Datta, New York, NY (US)

(73) Assignee: The City University of New York, New York, NY (US)

( * ) Notice: Subject to any disclaimer, the term of this patent is extended or adjusted under 35 U.S.C. 154(b) by 349 days.

(21) Appl. No.: 18/331,638

(22) Filed: Jun. 8, 2023

(65) Prior Publication Data

US 2024/0408391 A1      Dec. 12, 2024

(51) Int. Cl.
*A61N 1/36*            (2006.01)
(52) U.S. Cl.
CPC ..... *A61N 1/36025* (2013.01); *A61N 1/36034* (2017.08)
(58) Field of Classification Search
None
See application file for complete search history.

(56) References Cited

U.S. PATENT DOCUMENTS

| | | | |
|---|---|---|---|
| 11,285,319 B1* | 3/2022 | Hubbard | A61B 5/4812 |
| 2019/0151654 A1* | 5/2019 | Wingeier | A61N 1/3603 |
| 2021/0346689 A1 | 11/2021 | Wingeier et al. | |

FOREIGN PATENT DOCUMENTS

WO        2007138598 A2      12/2007

OTHER PUBLICATIONS

International Search Report and Written Opinion Issued in PCT Application No. PCT/US2023/26548, mailed on Feb. 20, 2024, 15 Pages.

* cited by examiner

*Primary Examiner* — Mallika D Fairchild
(74) *Attorney, Agent, or Firm* — Mintz Levin Cohn Ferris Glovsky and Popeo, P.C.

(57)                ABSTRACT

Methods, devices, and systems are described for closed-loop neuromodulation for control of a physiological state. The system includes an energy application system, a user device, a sensor, and a controller. The controller may be configured to select a state phase based on an engagement component. The controller may be configured to prompt at least one of the user device to present a cue to the subject or the energy application system to apply the electrical stimulation to the subject based on the selected state phase. The controller may be configured to measure the set of physiological reactions induced by the selected state phase. The controller may determine a subject bio-psychiatric therapeutic trajectory based on the measured set of physiological reactions from the subject, the subject bio-psychiatric therapeutic trajectory generated by mapping the set of physiological reactions from the subject to the state phase.

18 Claims, 18 Drawing Sheets

100

100

400

500

600

700

702

Measure the unsatisfying physiological reaction from the subject

704

Apply an electrical stimulation having a different modality than a first electrical stimulation

800

Determine a physiological reaction reactive to the state phase satisfies a disengagement threshold ⌐ 802

Interrupt the presentation of the state phase of the engagement component to the subject ⌐ 804

Prompt the subject to reengage with the engagement component ⌐ 806

900

| | |
|---|---|
| Prompt a computing device to present an engagement component having a timing of administering | 902 |
| Receive input corresponding to a timing of a next state phase | 904 |
| Determine whether the next engagement component is enabled based on the input | 906 |

1000

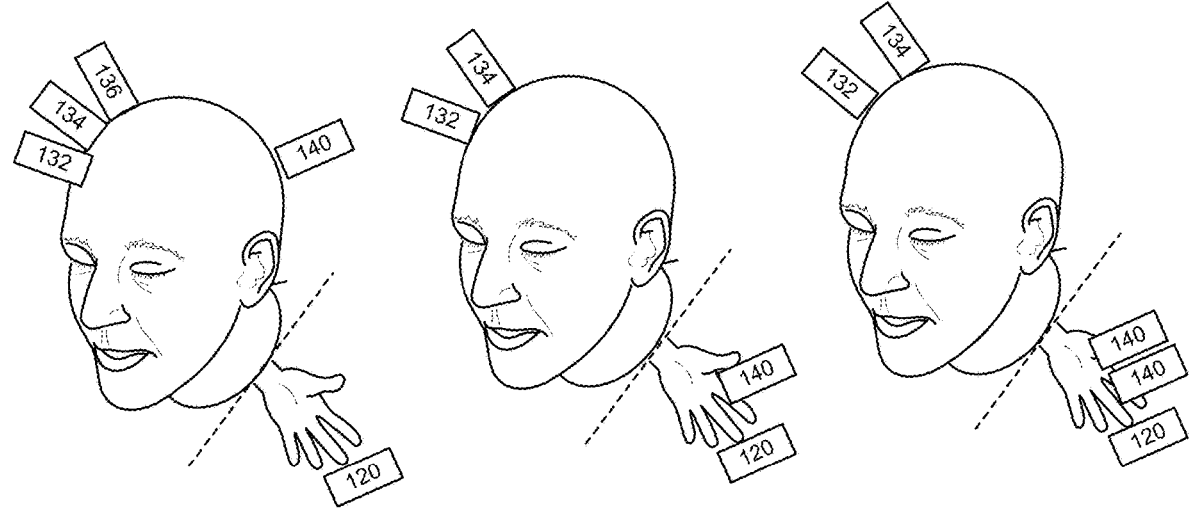
FIG. 11F　　　　FIG. 11G　　　　FIG. 11H

ENGAGEMENT COMPONENT SELECTION FOR CONTROL OF BIO-PSYCHIATRIC THERAPEUTIC TRAJECTORY (BTT)

TECHNICAL FIELD

The present disclosure relates generally to wellness, pain, mental health, neurological disease and, more particularly, to device-based interventions for optimal control of physiological state.

BACKGROUND

Various treatment modalities exist for remedying brain disorders. Brain disorders include neurological diseases affecting movement, such as Parkinson's disease, Huntington's disease, and Restless Leg syndrome. Brain disorders also include psychiatric diseases, such as depression, bipolar disorder, borderline personality disorders, anxiety disorders, behavioral disorders, emotional disorders, bipolar affective disorder, dissociation and dissociative disorders, eating disorders, obsessive compulsive disorder, and paranoia.

These treatment modalities vary in their efficaciousness. But they often suffer from several severe drawbacks. Each of these traditional treatment modalities and their associated limitations are described below.

One technique for controlling brain disease includes the use of drugs or chemical agents. Medical management using these techniques requires considerable iterations of adjusting dosages to achieve balance between efficacy and side effects. Variation, such as circadian and postprandial variations, causes fluctuation in symptoms. This variation results in alternating between "good" and "bad" periods during which a patient may not receive benefit.

Another approach for controlling brain diseases is tissue ablation. When prescribed, tissue ablation is commonly accomplished through stereotactic neurosurgical procedures, including pallidotomy, (sub)thalamotomy, and other lesioning procedures. These procedures have been found to be efficacious at times but they are irreversible and can lead to complications. In addition to posing risks that are inherent to neurosurgical operations, one key limitation is that tissue destruction is not reversible. As a result, improper removal of tissue cannot be later remedied.

Another approach for treating brain disorder is the electrical stimulation directed to a particular body region such as a brain target. For example, chronic mid frequency intracranial electrical stimulation has been proposed to mimic the effects of a tissue ablation. What is needed, therefore, is an apparatus and method for treatment of patients with brain disease or general mental health providing an optimal dose or intensity of treatment.

BRIEF DESCRIPTION OF THE DRAWINGS

The embodiments herein may be better understood by referring to the following description in conjunction with the accompanying drawings in which like reference numerals indicate identically or functionally similar elements, of which:

FIG. 11F depicts a computing device connected to receive input from the hand of the human patient and three energy-emitting devices and a sensor connected to the head of the human patient;

FIG. 11G depicts a computing device connected to receive input from the hand of the human patient, a sensor connected at the hand, and two energy-emitting devices connected to the head of the human patient;

FIG. 11H depicts a computing device connected to receive input from the hand of the human patient, two sensors connected at the hand, and two energy-emitting devices connected to the head of the human patient;

DETAILED DESCRIPTION

Figure 1A:
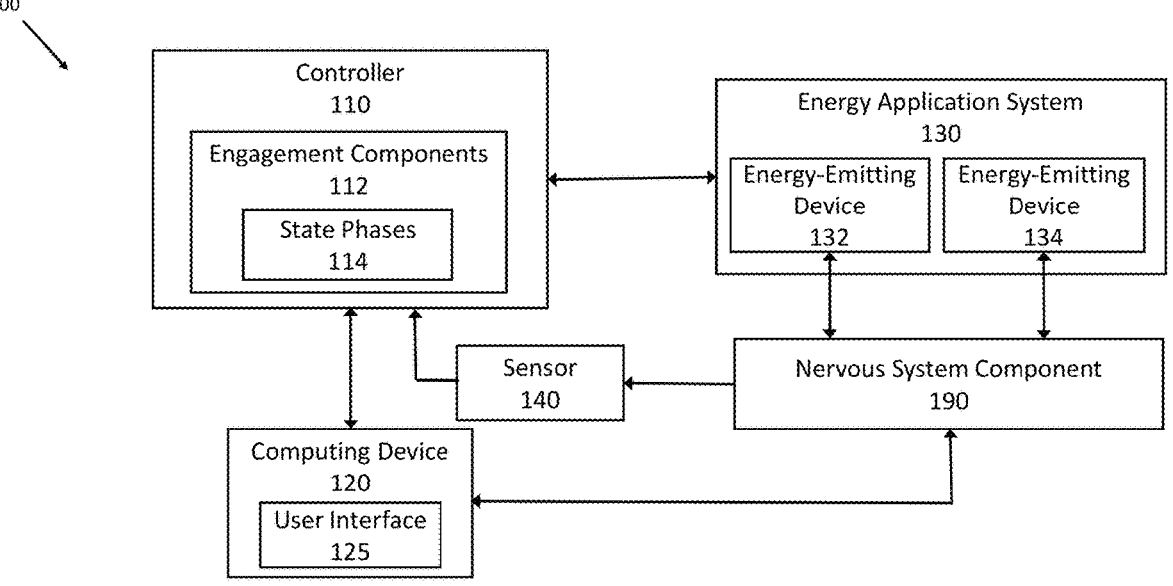
FIG. 1A depicts an example of a physiological wellness control system configured to suppress undesired physiological states in a subject having a nervous system component.

The methods, systems, and apparatuses described herein are for engagement component selection for control of bio-psychiatric therapeutic trajectory (BTT). In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

The present disclosure relates a neurological wellness control system for changing activity of any component or structure comprising the entirety or portion of the nervous system, or any structure interfaced thereto, generally referred to herein as a "nervous system component." The neurological wellness control system is configured to instruct the energy application system to generate neural modulation signals delivered to a nervous system component through one or more sources (e.g., surface or intracranial electrodes) to any portion of the body that influences the nervous system component in accordance with treatment parameters. The neurological wellness control system described herein is an interventional approach where the intervention(s) is not decoupled from the intended outcomes and is an apparatus and method for changing physiological state (including as relevant for patients with brain diseases of general mental health) by a system that couples the individual's physiological trajectory (against a desired trajectory) to selection intervention components (phase states). The intervention efficacy is then emergent based on both device and physiological interactions.

Treatment parameters may be derived from neural responses and/or previously delivered neural modulation signals sensed by one or more sensors in such a way that responsiveness to stimulation is detected. The treatment parameters may be configured to sense a particular characteristic indicative of a neurological or psychiatric condition or wellness state or another measurand indicative of these such as heart rate variability or vagal tone. Such neural control signals include any energy source waveform that enhances or inhibits cell activity. Specifically, the neurological control system may consider neural response in the form of the sensory feedback of any measurand as an indication or biomarker of neurological disease state and/or responsiveness to therapy. The neurological control system may consider neural responses and signals as biomarkers indicating responsiveness of the stimulation, and determinative of the treatment parameters based on control algorithm.

In one aspect, a neurological wellness control system for treating disease or enhancing brain wellness that provides stimulus intensity that may be varied is disclosed. The stimulation may be at least one of modulation, plasticity induction, activating, inhibitory, or a combination of the above at least one of neurologic, psychiatric, or wellness application. The brain wellness control system may treat neurologic diseases including, for example, COVID or other viral infection related morbidity, TBI, Parkinson's disease, Huntington's disease, rigidity, hemiballism, choreoathetosis, dystonia, akinesia, Parkinsonism, stroke, brain injury, bradykinesia, hyperkinesia, other movement disorder, epilepsy, or related seizure disorders, or any of these disorders as the particularly relate to children or older adults.

The neurological wellness control system may treat psychiatric diseases including, for example, major depression, bipolar disorder, other affective disorders, anxiety, phobias, schizophrenia, and multiple personality disorder. The brain wellness control system may treat psychiatric disorders including, for example, drug addiction or abuse, ADHD, aggression, impaired sexual behavior, borderline personality disorders, anxiety disorders, behavioral and emotional disorders in children, bipolar affective disorders, dissociation and dissociative disorders, eating disorders, obsessive compulsive disorder, paranoia, or any of these disorders as they particularly relate to children or older adults. The neurological wellness control system may provide brain wellness applications including, for example, sports performance enhancements, memory improvement, happiness and general well-being, focus, mental performance, cognitive skills, learning development, educational benefits, or training benefits.

In another aspect, the neurological wellness control system may modulate the activity of at least one brain or peripheral nervous system component, and include at least a stimulating electrode configured to attach to the subject head. The stimulating electrode may be configured and arranged to deliver a neural modulation signal to at least one of the brain or the peripheral nervous system component. The neurological wellness control system may include at least one detection device or sensor, each configured and arranged to sense at least one parameter, including but not limited to a measurand reflecting a physiological value such as heart rate variability or vagal tone or condition of the nervous system, which is indicative of at least one of brain state, a magnitude of symptoms or function, and a responsiveness to stimulation.

The neurological wellness control system may include a controller unit configured to record the parameters and instruct the stimulations of the stimulating electrodes. The neurological wellness control system may include any associated mechanical support apparatus, arranged and configured to generate said modulation signal based upon a measurand sensed by said at least one sensor or detection apparatus (which may be separate or embedded in the stimulation system) in response to a previously delivered neural control stimulation. The mechanical support apparatus can span the head or any body region where either control stimulation or measurand is applied or detected.

In another aspect, a method or apparatus for intentionally changing the activity of at least one physiological state such as a brain state is disclosed. The neurological wellness control system may include at least one means for delivering physiological control signals to said body system component; and means for sensing a measurand relevant to that control signal response. In one embodiment, the control signal delivery may include a method for generating said physiological control modulation signal, said generating may include a generating a conditioning stimulation signal configured for conditioning sensed physiological response signals (including a measure of responsiveness). Conditioning the sensed physiological response signals may include adjusting the conditioning stimulation signal with respect to at least one of amplification, convolution, machine learning, low-pass filtering, high-pass filtering, band-pass filtering, notch filtering, root-mean square calculation, mapping, warping, referencing against a library, power calculation, rectification, envelope determination, and rectification. The neurological wellness control system may be configured to perform signal processing for processing said conditioned sensed physiological response signals to determine present physiological system states or predicted physiological system states. The neurological wellness control system states and predicted physiological system states may include, for example, a single or plurality of brain states, a single or plurality of disease states, or a single or plurality of mental health conditions. The neurological wellness control system may include a logic system or controller configured to adjust physiological modulation signals in response to sensed measurand and a calculated responsiveness.

Advantageously, aspects of the neurological wellness control system are capable of incorporating quantitative and qualitative measurements of patient symptoms, heart rate variability, vagal tones, and brain network circuitry functions in the regulation of treatment control signal.

The neurological wellness control system is configured to control the energy application to compensate for predictable or measured fluctuations in symptoms, cognitive functions, neuromotor load functions, physiological functions, and a patient-desired state. Predictable or measured fluctuations may include, for example, fluctuations in reflecting exercise, movement, the circadian cycle, sleep, rest, postprandial levels, symptoms, diet, environment, engaging in activity, plasma levels of drugs, or other detectable agents.

The neurological wellness control system may be configured to respond to patient symptomatology, as brain dysfunction typically abates during specific phases of the day. The neurological wellness control system may be configured to predict future symptoms, cognitive dysfunction, neuromotor dysfunction, and energy treatment regime requirements. Predictions supporting energy optimization may be based on predetermined, learned, and real-time sensed measurands or parameters as well as input as provided from the patient, operator, physician or other person or system.

The neurological wellness control system may perform pre-programmed, pre-automated, or semi-automated determinations of the optimum treatment or intervention, each in the current time or in a predicted future state. By sensing and quantifying the appropriate features as obtained from the described measurand and comparing them to a desired state or a desired responsiveness. The mental health, physiological state, or disease state may be represented as a single value, multiple values, or a vector or matrix of values. A multi variable optimization algorithm may be employed with appropriate weighting factors that would be considered in the brain health control system. Automated or semi-automatic control and optimization of stimulation energy parameters may streamline the achievement of satisfactory outcomes of the patient, and enable achievement of performance not otherwise possible, reducing the time and number of interactions required between the patient or doctor and the device. This optimization may include, for example, selection of electrode polarity, electrode configurations, electrode positions, stimulating parameter intensities, stimulating parameter waveforms, sequences of activation, temporal profile activation, use of duty cycles, initial energy stimulation settings, and other stimulation parameters.

The neurological wellness control system may perform measurand processing, transmission, and display through a user interface to the patient, operator or clinicians. The patient, operator, or clinicians may augment their interface with the brain health control system by selecting preferred outcomes, stimulation energy configurations, and other parameters such as duty cycle. Measuring signals of their processed derivatives (features) may be provided by the brain health control system to the operator, patient or clinician using a specifically designed and configured interface including, but are not limited to, a happiness measurement, a depression inventory score, a heart rate variability, tremor estimates, electromyography (EMG) signals, EEG signals, accelerometer signals, acoustic signals, peripheral nerve signals, cranial nerve signals, cerebral or cerebellar cortical signals, brain injury, pain, signals from the motor or sensory cortex or prefrontal cortex, signals from deep brain regions such as the basal ganglia, signals from other brain or spinal cord structures including the dorsal column or roots or nerves, motion trackers, GPS, galvanic skin response, accelerometers, and other physiological or brain signals. The neurological wellness control system will further leverage signals from the environment such as temperature and pressure. The system will further leverage information from subject state or subject activity such as performance on an associated or prescribed task, such as a learning task.

The neurological wellness control system may optimize the efficiency of energy used in the treatment given to the patient. Stimulation intensity may be minimized using a so-called a "light touch approach" so as to provide the minimum but effective level of treatment energy necessary to achieve the desired outcomes without excessive energy delivery leading to delivering unnecessary overtreatment. Further features and advantages, as well as the structure and operation of various embodiments, are described in detail below with reference to the accompanying drawings.

FIG. 1A depicts an example of a physiological wellness control system 100 configured to suppress undesired physiological states in a subject having a nervous system component 190. The physiological wellness control system 100 may include a controller 110 communicatively coupled to a computing device 120, an energy application system 130, and a sensor 140. The computing device may be communicatively coupled to the nervous system component 190 and the controller 110. The energy application system 130 may be communicatively coupled to the nervous system component 190 and the controller 110. The sensor 140 may be communicatively coupled to the nervous system component 190 and the controller 110. The physiological wellness control system 100 should be responsive to changes in symptoms and prevent or minimize alternations between states of overtreatment and undertreatment. The physiological wellness control system 100 should also be capable of anticipating future changes in symptoms and brain functionality, so that it is responsive to such changes when they occur.

The physiological wellness control system 100 may integrate an 1) energy application system 130 (e.g., electronic waveform generator) configured to change at least one aspect of the nervous system function; 2) a head gear configured to position an energy emitting device 132 on the head in a manner that supports directionality of the energy to one or more targets of the nervous system function; 3) at least one sensor 140 configured to detect or measure at least one physiological function; 4) a controller 110 configured to process signals from the sensor 140 and update the function of the energy application system 130; and 5) a computing device 120 with a user interface 125 configured to engage a subject in a task or an activity. The physiological wellness control system 100 may be configured to provide updates to the energy application system 130 or to the computing device 120 with a user interface 125 based on the sensor 140 performance and/or the task performance by the user. The software platform integrated into the computing device 120 may be configured to engage the subject. The computing device 120 can be a stand-alone device, a smartphone or mobile device having an app, a software application or a web-based interface as the user interface 125.

The controller 110, may be affixed to the housing and coupled to the energy application system 130. The controller 110 may be configured to receive digital signals associated with the electrical signals produced by the sensor 140 and to determine the heart rate variability based on the digital signals. The controller 110 may be configured to transmit an activation signal to activate the energy application system 130 based on whether the determined heart rate variability satisfies heart rate variability feedback criteria. A user control coupled to the controller 110 may enable a user to select an operational mode having particular heart rate variability feedback criteria from a plurality of operational modes under which the controller 110 operates.

In some embodiments, the controller 110 automatically adjusts stimulation parameters based on historically stored datasets from matching populations with disorders and administers dose to the patient. The controller may, in real time, monitor variant neurobiological signals and update the BTT based on a physio-behavioral model. In some embodiments, the controller 110 identifies a neurobiological signal, matches the template with historically stored signal database, and generates an updated neurostimulation waveform for stimulation. In another embodiment, the controller 110 categorizes the sensed neurobiological oscillation into multitudes of characteristic brain activity related oscillations. The controller 110 may be referred to as the neural controlling apparatus, a brain wellness control system, a brain health control system, or a hear rate variability signal feedback monitor system. In some embodiments, the hardware, communicative abilities, and functions of the controller 110 may extend to and/or be shared with the hardware, communicative abilities, and functions found in other components of the physiological wellness control system 100, such as the computing device 120, the user interface 125, the energy application system 130, and the sensor 140. The hardware, communicative abilities, and the functionalities of the physiological wellness control system 100 and its components (e.g., the computing device 120, the user interface 125, the energy application system 130, and the sensor 140) may extend to and/or be shared with in the controller 110.

Still referring to FIG. 1A, the computing device 120 with a user interface 125 may be configured to engage the subject by displaying an engagement component 112. The computing device 120 with a user interface 125 may be configured to present cues to the subject via the user interface 125. engagement component 112 may be played to the subject in sequence by the computing device 120 with a user interface 125. There may be 4, 10, 50, or 100 engagement components 112. For example, with four engagement components 112, the engagement components 112 may be played in sequence on a Monday, Tuesday, Wednesday, and Thursday. For example with 50 engagement components 112, an engagement component may be played one weekday for 10 consecutive weeks. Depending on the protocol, there may be or more than day between the engagement components 112. For example, a 10 engagement component protocol may be provided over about 20 days with an engagement component provided every other day. Engagement components 112 in which subjects are expected to watch and engage with the component may be referred to as engagement components 112. An engagement component 112 may be a guided meditation, music, or a task. The user interface 125 may be referred to as the software. The user interface 125 may include a vibration output device to generate energy to indicate a user is to perform an action. The vibration output device can be, for example, a mobile computing device, a transducer mounted to the body or clothing, a keyboard or mouse, a plate interface, a car piece, a belt or belt attachment, a phone, a watch, and/or the like.

The physiological wellness control system 100 may include an energy application system 130. The energy application system 130 may be configured to configured to apply an electrical stimulation to a subject head of a subject for inducing a physiological reaction in the subject, the energy application system 130 having at least a first energy-emitting device and a second energy-emitting device that support directionality of the electrical stimulation across the subject head. the first energy-emitting device and the second energy-emitting device are electrodes, and wherein the sensor 140 may be configured to measure at least one of a DC component of a transimpedance measurement or an AC component of the transimpedance measurement representative of the physiological reaction, and wherein the sensor 140 may be configured to measure the transimpedance across at least the first energy-emitting device and the second energy-emitting device coupled to the subject head, the transimpedance representative of a coupling between the energy application system 130 and an electro-impedance of the subject. The energy application system 130 may be configured to generate a DC component feature and an AC component feature Still referring to FIG. 1A, the energy application system 130 may be configured to administer dynamic stimulation dose to the central nervous system in a precise manner by specifically relying on instantaneous biological feedback. The energy application system 130 may be a closed loop electric waveform generator (EWG). The energy application system 130 may apply a stimulation waveform through at least one stimulating electrode based on at least a portion of the neurobiological signal sensed by at least one sensing electrode, which is remotely transmitted to the cloud storage in real-time. The stimulation intensity may be incrementally ramped up or down based on the incoming neural signal or historically stored signals. The energy application system 130 can transition from alternating current to direct current for a given duration of alternating current stimulation and cycle by modulating the duty cycling. The proposed engagement component selection system for controlling a BTT implements more than one stimulation modality by continuously monitoring neurobiological signals and adjusting parameters to bring desired brain therapeutic benefit. The energy application system 130 may generate a closed-loop waveform when the spectral density is within the limit of current power threshold value. The closed-loop electric waveform generator (EWG) may include a configured user interface to output stimulation parameters and input various neurophysiological datasets from patients with or without performing audio-visual tasks. The EWG system generates a plurality of waveforms of desired shape, frequency, pulse width, duty cycle, phase, and magnitude. In one embodiment, a portion of the system incorporating non-invasive or minimally invasive conductive coil or metal contacts is either implanted between skin and skull or over the skin generates either DC or AC electrical or magnetic field stimulation waveform. the closed-loop electric waveform generator system provides energy to the brain through at least one implantable contact that provides a conductive path through the resistive skull to a plurality of brain locations. In yet another embodiment, the energy applied to the body is internal and is administered using an implantable pulse generator and lead, where the pulse generator is implanted in different parts of the body. The neurostimulation system identifies and triggers administration of stimulation in phase with a range of sensed slow-wave neural oscillations.

In one embodiment, the energy application system 130 may include an external headset with incorporated waveform generator and/or ultrasound transducer, or an external set up using handheld RF generator or a magnetic field generator to generate a stimulation waveform. The neurostimulation headset may be configured to apply ultrasound waveform first, then adjust the waveform based on the measured response from the brain in response to the initially applied waveform, and finally dynamically adjust the first waveform to generate the following waveforms. The applied low intensity current can be at least 10 microamps. The applied low intensity current (LIC) can be between 10 microamps to 10 milliamps. The LIC can be applied with metal electrodes, carbon rubber electrodes, fabric electrodes, or mixed polymer electrodes. The LIC can be applied with electrolyte gel, saline, or no interface between the electrode and the head. The sensor 140 is at least one of the first energy-emitting device and the second energy-emitting device coupled to the subject head. The energy application system 130 may referred to as a tactile actuator device, a transimpedance circuit, a stimulator, or a vibration output. In some embodiments, the controller 110 may be coupled to a vibration output device. The vibration output device may be an energy-emitting device 132. The controller 110 may be configured to transmit an activation signal to activate the vibration output device based on whether the determined heart rate variability satisfies heart rate variability feedback criteria. The controller 110 may be configured to receive digital signals associated with the electrical signals produced by the sensor 140 and determine the heart rate variability based on the digital signals in response to the vibration output device emitting energy.

Still referring to FIG. 1A, the physiological wellness control system 100 may include a sensor 140 configured to couple to the subject to detect at least one feature of the physiological reaction of the subject. Sensor 140 may be configured to measure responses to any of the following in isolation or combination: electrostatic discharge and induced electromagnetic interference, any activity related oscillation detector, an electric waveform generator (EWG) and escalator, an electric waveform timer, waveform sequencer, and transducer driver. The sensor 140 may include a plurality of sensing electrodes is deployed to sense the neurobiological signals. The sensor 140 may include a plurality of sensors positioned at different locations of the body to sense the level of neurotransmitter and transmits it to the decoder. The brain signal recording is transmitted wirelessly by at least one implanted compartment through coil or metal contacts and is received by non-invasive external electrodes or a recording medium. In some specific embodiments, the few sensed neurotransmitters are, but not limited to dopamine, serotonin, or norepinephrine. The cephalic cardiographic signal can be acquired on live patients' head or at cephalic locations. The signal can be acquired with at least two sensors placed on the head. The signal can be acquired with between 2-128 sensors on the head. The signal can be acquired at the site of low intensity current (LIC) application or at cephalic locations distance from the site of low intensity current application (LIC). The sensors 140 can include metal electrodes, carbon rubber electrodes, fabric electrodes, or mixed polymer electrodes. The sensors 140 that acquire the signal can have electrolyte gel, saline, or no interface between the sensor 140 and the head. The sensors 140 will acquire underlying brain and physiological activity. The method will extract signals between 0-100 Hz. The sensor 140 may be referred to as the wearer's electronics module, the wearer's electronics system, the body system component, headgear, a light base sensor, a dual-pole sensor, or a hand-held device.

Still referring to FIG. 1A, the physiological wellness control system 100 may be communicatively coupled to the nervous system component 190 of the subject. The nervous system component 190 of the subject may include the brain, spinal cord, peripheral nerve, cranial nerve, or any other part of the body configured to receive energy from the energy application system 130 and read an electrical signal or other biopotentials using the sensor 140. In an aspect, a method for effectively recording biopotentials and applying stimulation may be performed by the physiological wellness control system 100. Biopotentials can be acquired through electrodes placed on the body. Analyzing the bio-signal or biopotential may entail correlating the bio-signal with a certain mental state (by BTT) and providing the subject with feedback that includes at least one suggestion for enhancing the subject's mental condition. The feedback can be tactile, visual, electrical, ultrasound, light-based, magnetic waves or pulses, or audible. Each electrode, in one embodiment, has at least one pin with a first free end that includes a skin contact interface and a second end that is coupled to the energy application system 130. Each electrode, in one embodiment, has at least two pins, one of which has a skin contact interface and the other of which is coupled to the energy application system 130. The electrodes may be at least three flexible branches that are resiliently deformable in one embodiment. The at least three flexible branches may be composed of polypropylene or a silicon-based polymer in one embodiment. A ground electrode, a reference electrode, and at least one acquisition electrode may be among the at least three electrodes in one embodiment.

The nervous system component 190 of the subject or the subject skin may be prepared or treated prior to applying the electrode. The nervous system component 190 is not limited to a brain or a neurological tissue and can be any tissue in the body which includes extensions of the nervous system, excitable tissue, support tissue of the nervous system including mechanical or transport tissue, end organ sensors of the nervous system, muscle tissue, or biochemical or biomechanical process that influence the function of the nervous system. Various diseases, muscle pain, or inflammatory issues may be treated by stimulating the nervous system component 190. In one embodiment, the skin may be pre-treated with exposure to sanitizing agents; these can include sanitizing alcohols, sanitizing surfactants, or hydrogen peroxides. In one embodiment these sanitizing agents can be applied directly to the skin area for preparation, while immersed in dilution agents or while applied to cloths or disposable tissue gauze or fabrics. In one embodiment, pretreatment of the skin can include exposure to energy sources like light sources covering different frequencies of the electromagnetic spectrum, heat sources that warm to skin, or vibration or vibrotactile sources.

The controller 110 may be able to generate a dose optimization for a closed-loop electric waveform generator. The dose optimization includes monitoring patient's neurological disorder, administering stored waveform as a first dose when neurological disorder is detected, reanalyzing the patient for substantial activity indicating a neurological disorder, determining whether the dose was optimal (over or under threshold), and then manipulating the waveform parameters.

Still referring to FIG. 1A, the controller 110 may be able to assess whether the stimulation waveform was optimal or not includes monitoring whether the patient has substantial activity indicating neurological disorder response and if not the case, reassess if the patient received the first stimulation dose. In another embodiment, when the stimulation waveform is overdose, the stimulation parameter is decreased (the new state phase), and is stored as a new stimulation waveform after recording. In yet another embodiment, when the stimulation waveform is underdose, the stimulation parameters are increased (the new state phase) and are also stored as a new waveform after recording. In still another embodiment, the upgrading or downgrading of stimulation parameters is avoided in case the stimulation waveform is optimal.

The controller 110 may be able diagnose a neurological disorder by connecting the closed-loop electric waveform generator (EWG) to an adaptive stimulation controller, connecting the system to a patient, wiring the remote terminals to the adaptive stimulation controller, querying information about the patient and the controller 110 via a graphical user interface, and regulating the stimulation parameters of the closed-loop electric waveform generator to optimize the adaptive stimulation controller for wide range of patients. The neurostimulation therapy is administered in temporal sequential sessions of state phases based on the recorded neurobiological signal, using sets of one or multiple electrodes, and is continuously updated based on the following new sets of neurobiological signals.

Still referring to FIG. 1A, the controller 110 may maintain optimized dosage and tolerability profile for efficacy of neurostimulation using an adaptive logic waveform tailored (at least in one state phase) from historically stored participant's feedbacks, real time system impedance (skin impedance, electrode impedance), and biomarkers (EEG, EKG, galvanic skin response, eye tracking, etc.) In one embodiment, the system further processes the stimulation waveform data via a cloud-based machine learning step to train, test, and cross-validate the target intensity for individualized neurostimulation. In some embodiments, the system has built-in artifact cancellation techniques to ensure recording of the first noise-free neurobiological signal for later dynamic adjustment of stimulation parameters. In an embodiment, the adaptive controller of the closed-loop neurostimulation system determines the absolute phase threshold value, based on multitudes of prior works.

One preferred embodiment for the controller 110 is a micro-controllers or computers. However, digital electronics components in the form of integrated circuits (ICs) such as a microprocessor and support circuits including PROM, RAM, ROM forming program storage means and data storage means, I/O, bus controllers forming interface circuitry can be used to create a self contained system controller which can be housed in a portable enclosure and mounted onto a headgear or inside a hand-held device. The microprocessor, EPROM, RAM, ROM, components are available from known sources along with fabrication and programming guidelines and are understood in the electronics arts. Such a self-contained controller can be battery powered and portable. In addition, digital processing components allow the implementation of flexible engagement components 112 and BTT value computations which increase the usefulness of the apparatus.

In one embodiment, the components of an engagement component or closed loop neuromodulation system are virtually assembled in a software platform to receive, store, adjust, and administer dose based on different patient-specific bio physiological recordings.

Still referring to FIG. 1A, the components of engagement components or closed-loop neuromodulation systems are assembled in integrated circuit boards or 3D printed platforms and remote computing devices to receive, store, adjust, and administer dose based on different patient-specific bio physiological recordings.

In one embodiment, there is one or more processors and a steady computing medium that has executable information encoded, which upon execution, perform multiple operations utilizing one or more processors. Physiological wellness may include applications in neurological wellness, treatment of brain disorders, treatment of neurological disorders, treatment of psychological or psychiatric disorders, reduce of pain, tremor, or other undesired sensations, reduction of seizures, reduces of pathological tissue size or promotion of tissue healing, enhancement of mental performance, increasing memory, focus, or cognition, enhancing sports performance, increasing endurance, reducing fatigue, improving quality of life, reducing symptom burden, increasing life expectancy, reducing risk to pregnant individuals or their fetus, enhancing relaxation, and/or enhancing the amount of quality of sleep.

Figure 1B:
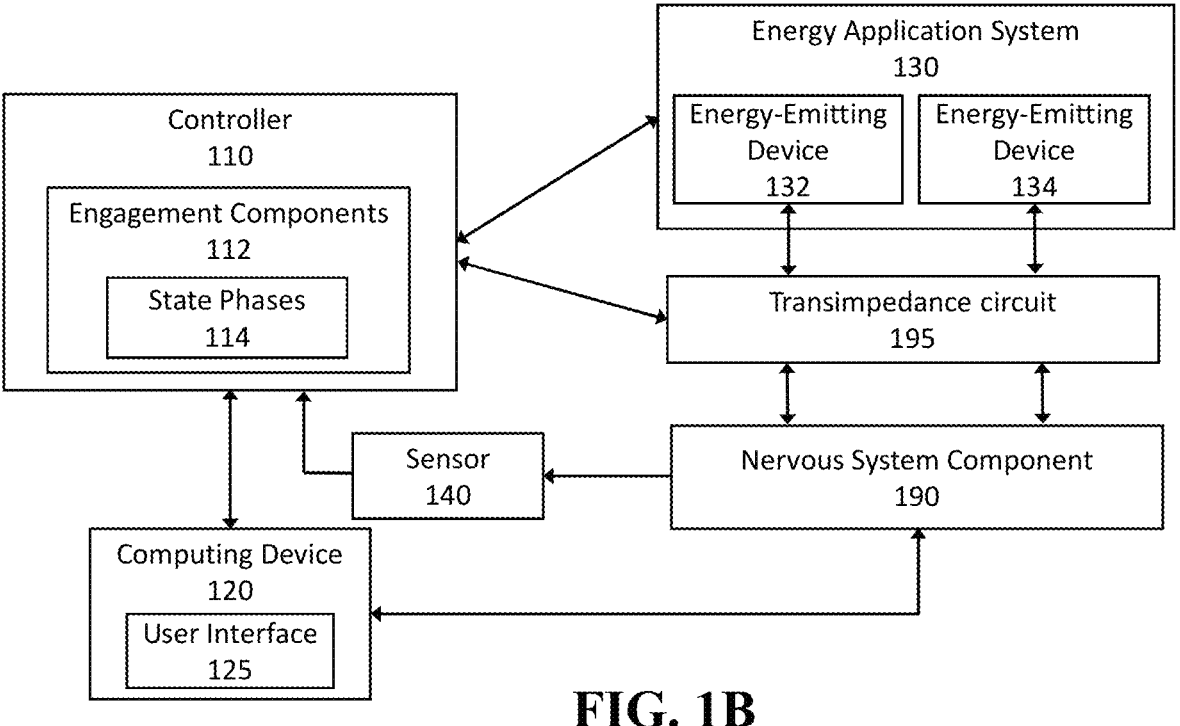
FIG. 1B depicts an example of a physiological wellness control system with a transimpedance circuit configured to detect various interactions between the physiological control system and the nervous system component.

FIG. 1B depicts an example of a physiological wellness control system 100 with a transimpedance circuit 195 configured to detect various interactions between the physiological wellness control system 100 and the nervous system component 190. The transimpedance circuit 195 may be communicatively coupled to the energy application system 130 and the nervous component system 190.

The transimpedance circuit 195 may be configured to detect and measure the transimpedance generated across the energy application system 130, the energy-emitting device 132, the energy emitting device 134, the nervous system component 190, and the sensor 140. The transimpedance circuit 195 is configured to measure the combination of various impedance interactions between the energy application system 130, the energy-emitting device 132, the energy emitting device 134, the nervous system component 190, and the sensor 140 with a directional vector associated with one or more impedances. In some embodiments, the measured transimpedance of the various impedance interactions across the energy application system 130, the energy-emitting device 132, the energy emitting device 134, the nervous system component 190, and the sensor 140 may be represented by a multi-dimensional array to capture the directionality and the magnitude of the impedances between the nodes of the different system components (e.g., the energy application system 130, the energy-emitting device 132, the energy emitting device 134, the nervous system component 190, and the sensor 140). In some embodiments, the controller 110 may perform linear transformations or transformational multiplication, division, of the multi-dimensional arrays to extract features or trajectories of the subject physiological response. The controller 110 may convert the measurements to a different domain (i.e., the frequency domain via Fourier transform) to determine the features of the subject physiological response. The measurements may be represented by complex numbers.

In some embodiments, the transimpedance circuit may be a separate circuit from the energy-emitting device 132 and the energy-emitting device 134. The transimpedance circuit may include a voltage detection device and a resistance detection device for calculating the voltage and resistance at various nodes (e.g., the energy application system 130, the energy-emitting device 132, the energy emitting device 134, the nervous system component 190, and the sensor 140) across the physiological wellness control system 100. The controller 110 may be configured to determine the voltages and resistances at each of the various nodes using the voltage detection device and the resistance detection device. The controller 110 may calculate the combination and various interactions of impedances between the energy application system 130, the energy-emitting device 132, the energy emitting device 134, the nervous system component 190, and the sensor 140 with a directional vector associated with one or more impedances.

In another embodiment, the energy-emitting device 132 and the energy-emitting device 134 may change the transimpedance across the various nodes (e.g., the energy application system 130, the energy-emitting device 132, the energy emitting device 134, the nervous system component 190, and the sensor 140) while the transimpedance circuit 195 may be configured to monitor and measure the transimpedance. The energy-emitting device 132 and the energy-emitting device 134 may change the transimpedance across the various nodes based on the measured transimpedance from the transimpedance circuit 195. Additionally, and/or alternatively, the transimpedance circuit 195 may include an AC signal generator for independently determining the transimpedance across the nodes (e.g., the energy application system 130, the energy-emitting device 132, the energy emitting device 134, the nervous system component 190, and the sensor 140). For example, the energy application system 130 may apply (via the energy-emitting device 132 and the energy-emitting device 134) 10 mA DC to the nervous component system 190 and the transimpedance circuit 195 may apply an additional 10 kHz AC signal at 0.1 mA to determine the transimpedance beyond just the DC component.

Figure 1C:
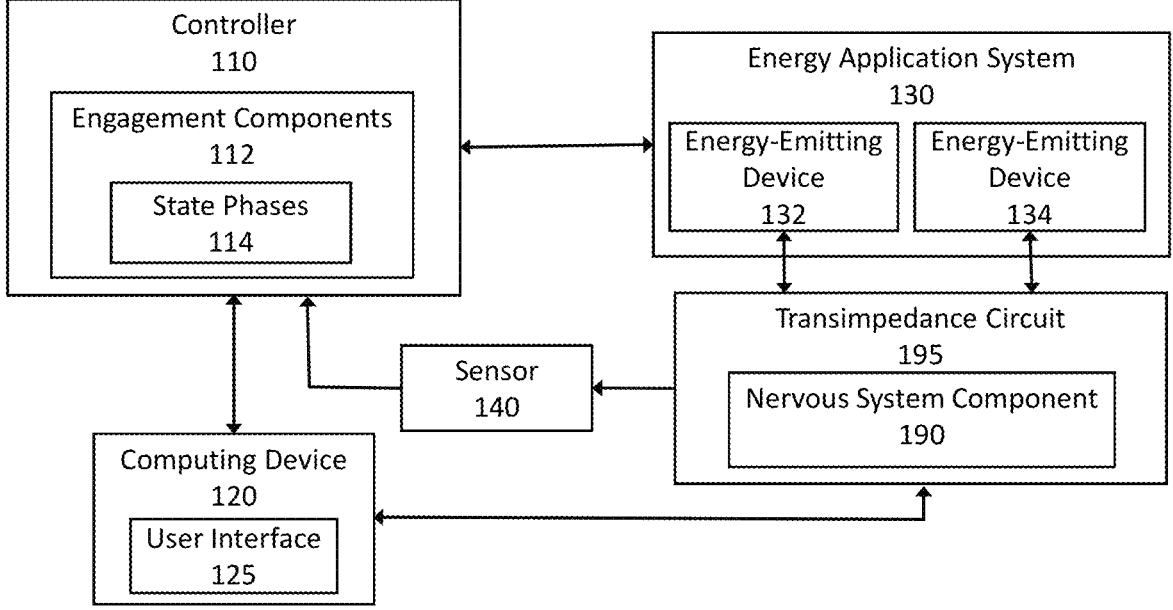
FIG. 1C depicts an example of a physiological wellness control system with another transimpedance circuit configured to detect various interactions between the physiological wellness control system and the nervous system component.

FIG. 1C depicts an example of a physiological wellness control system 100 with another transimpedance circuit configured to detect various interactions between the physiological wellness control system 100 and the nervous system component 190. The transimpedance circuit 195 may be communicatively coupled to the energy application system

130, the energy-emitting device 132, the energy emitting device 134, the nervous system component 190, and the sensor 140. The transimpedance circuit 195 may isolate the energy application system 130, the energy-emitting device 132, the energy emitting device 134, and the sensor 140 from a direct electrical connection to the nervous system component 190. The transimpedance circuit 195 may be configured to generate destructive voltage/current waveforms to cancel out impedance across the various nodes (e.g., the energy application system 130, the energy-emitting device 132, the energy emitting device 134, and the sensor 140) in the physiological wellness control system 100. The destructive voltage/current waveforms can isolate noisy transimpedance between the components of the physiological wellness control system 100 and the nervous system component 190.

The transimpedance circuit 195 may be configured to generate a DC signal and an AC waveform to eliminate errant transimpedance measurements detected between the nodes. The transimpedance circuit 195 may isolate the nervous component system 190 to eliminate noisy DC or AC components across the nervous component system 190. In some embodiments, the transimpedance circuit 195 can amplify or create constructive waveforms or DC signals that correct the current/voltage from the energy application system 130. Additionally, and/or alternatively, the transimpedance circuit 195 may be configured to create constructive DC signals or AC waveforms to modify or compensate a particular transimpedance measurement across the nervous component system 190. The transimpedance circuit 195 can generate AC signals or DC signals that alters the subject bio-psychiatric therapeutic trajectories.

Figure 2:
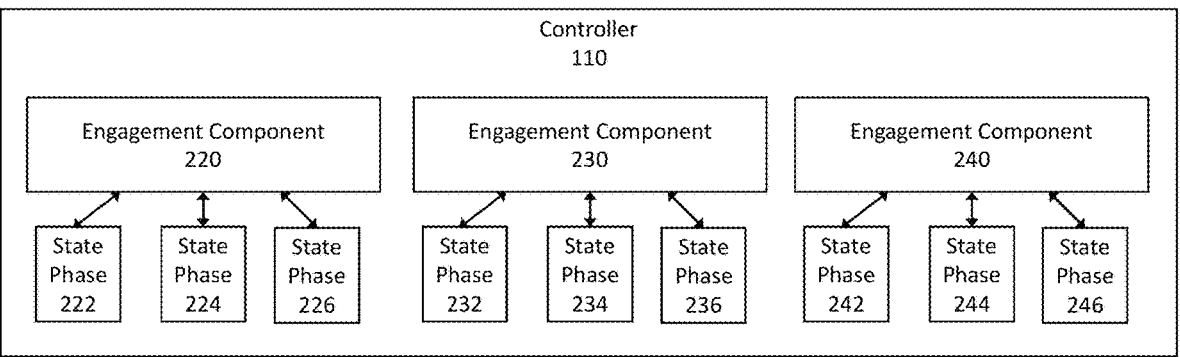
FIG. 2 depicts an example of a physiological wellness control system configured to select an engagement component including a set of state phases to be applied to the subject.

FIG. 2 depicts an example of a physiological wellness control system 100 configured to select an engagement component including a set of state phases 114 to be applied to the subject. The engagement component may include at least one of a guided meditation, music, or a task. The engagement component may be configured to dynamically determine the state phase from the set of state phases 114 based on subject attention to a previous state phase.

Each engagement component 112 may be further divided into phases. The phases may be separated at distinct times within the engagement component. Each engagement component may have one or more phases. These phases may represent distinct stages within the engagement component where subject state is expected to change. These phases are therefore called state phases 114. An engagement component can have 2, 5, 10, 100, or 1000 state phases 114. For example, engagement component 220 can have state phase 222, state phase 224, and stage phase 226. Similarly, engagement component 230 can have state phase 232, state phase 234, and stage phase 236. Similarly, engagement component 240 can have state phase 242, state phase 244, and stage phase 246.

State phases 114 may repeat. For example an engagement component can have 10 state phases 114 where the 1st, 5th, and 10th state phase are the same. The sequence of stage phases 114 in an engagement component may form a series of blocks. Each block corresponds to one state phase 114. The timing of the block indicates the timing of each state phase 114. The time of all the phase state blockers may be combined in the timing of the engagement component 112. For example, ten state phases 114, each lasting 10 minutes, produces an engagement component duration of 100 minutes. Twenty state phases 114 each lasting 1 minute, produces an engagement component duration of 20 minutes The device may be preloaded with a set of state phase (such as a, b, c, d) and the selection of state phases 114 and their sequences may be determined by the program. The state phases 114 may be presented by the computing device 120 to the user The controller 110 may calculate a rate of change of the physiological reaction in the subject in response to the state phase having a duration greater than 100 seconds and including at least 10 synchronized audio or visual cues. The rate of change of the physiological reaction may include a change in a measured parameter over time or a change in a measured parameter with respect to another measured parameter. The controller 110 may calculate a difference between the rate of change of the physiological reaction in the subject and a rate of change of the physiological reaction in a set of healthy subjects responding to the state phase having the duration greater than 100 seconds and including at least the 10 synchronized audio or visual cues. The difference may further include an intensity of a physiological reaction, a transformation of the physiological reactions from one mathematical domain to another mathematical domain, and calculating a difference between an expected physiological reaction and an actual anticipated reaction. The controller 110 may prompt the energy application system 130 to update an electrical feature of the electrical stimulation applied to the subject. In some embodiments, a machine learning model or an artificial intelligence may select the electrical features of the electoral stimulation based on the difference and rate of change.

The controller 110 may calculate a rate of change of the physiological reaction in the subject in response to the state phase having a duration greater than 220 seconds and including at least 12 synchronized audio or visual cues. The controller 110 may calculate a difference between the rate of change of the physiological reaction in the subject and a rate of change of the physiological reaction in the set of healthy subjects responding to the state phase having the duration greater than 220 seconds and including at least the 12 synchronized audio or visual cues. The controller 110 may prompt the energy application system 130 to update an electrical feature of the electrical stimulation applied to the subject in response the difference between the rate of change of the physiological reaction in the subject and the rate of change of the physiological reaction in the set of healthy subjects satisfying a difference threshold.

In some embodiments, the cues corresponding to the state phase are updated a peak rate between 20 Hz and 220 Hz, with at least one period where the state phase is not updated lasting greater than 1 second. The output of the energy application system 130 may update at a rate 0.1 to 18 times the cue update rate. In some embodiments, the cues corresponding to the state phase are updated at a cue update rate between 0.001 Hz and 1 Hz. The state phase may have at least one period that is not updated lasting greater than 10 seconds. The output of the energy application system 130 may update at a rate 0.1 to 18 times the cue update rate.

Still referring to FIG. 2, if the engagement component 112 is a guided meditation, the state phases 114 represent distinct times in the guided meditation. If the engagement component is a task, the state phases 114 may represent distinct sub-tasks. There may be distinct stage phases 114 with distinct guided meditation. There may be a state phase 114 with a first guided meditation and a separate state phase with a second guided meditation. The state phases 114 may differ in the guided meditation provided to the subjects.

The state phase may be selected from pre-determined set. In one embodiment there are at least two state phases 114 in an engagement component and each state phase can be selected from a set of six state phase options (a, b, c, d, e, f). In one application the sequence is a and then b. In one application the sequence is a and then a. In one application the sequence is a and then f. In one application the sequence is b and then c. In one application the sequence is c and then d.

The state phase set can consist of the following configurations:

A: Guided meditation 1, no stimulation, heart rate variability biomarker. B: Guided meditation 2, tDCS stimulation, heart rate variability biomarker. C: Guided meditation 2, tDCS stimulation, heart rate variability biomarker. D: Guided meditation 3, no stimulation, heart rate variability biomarker. E: Guided meditation 4, tDCS stimulation 2, heart rate variability biomarker. F: Guided meditation 4, no stimulation, heart rate variability biomarker The engagement component can include 4, 6, or 10 state phases 114 with state phases 114 selected from these options. For example, A, B, C, D. A. A. For example, A, A, B, E, F, F. The tDCS may be substituted with tACS. The tACS may be 0.1-500 Hz. The tACS may be high frequencies with a 1-20 kHz carrier. The tACS may have very high frequencies with a carrier of 10 kHz to 1 MHz. A very high tACS carrier frequency can be 20 kHz, 50 kHz, 120 KHz, or 330 kHz. The intensity of stimulation can be 0.01 mA to 30 mA. The stimulation can be 1 mA or 2 mA. tDCS stimulation 1 may be 1 mA and tDCS stimulation 2 may be 2 mA. Each state can last a duration or 0.01 seconds to 60 minutes. The state phases 114 can have the same or different durations. One or more state phases 114 can have a duration of 5 minutes. One or more state phases 114 can have a duration of 10 minutes.

Still referring to FIG. 2, each state phase of the set of state phases 114 may be divided into multiple state phases 114 to provide a new set of instructions to invoke a different physiological response corresponding to a change in a plurality of historical bio-psychiatric therapeutic trajectories. The new set of instructions may be related to the engagement component and that is selected based on subject attention.

The state phase set can consist of the following configurations:

A: Guided meditation 1, no stimulation, heart rate variability biomarker; B: Guided meditation 2, high frequency stimulation, heart rate variability biomarker; C: Guided meditation 2, tACS stimulation, heart rate variability biomarker; D: Guided meditation 3, no stimulation, heart rate variability biomarker; E: Guided meditation 4, very high tACS frequency stimulation 2, heart rate variability biomarker; F: Guided meditation 4, no stimulation, heart rate variability biomarker.

The state phase set can consist of the following configurations:

A: Guided meditation 1, tDCS, heart rate variability biomarker and bioimpedance; B: Guided meditation 2, tACS, heart rate variability biomarker; C: Guided meditation 2, tDCS stimulation, heart rate variability biomarker and bioimpedance; D: Guided meditation 3, tDCS stimulation, heart rate variability biomarker; E: Guided meditation 4, very high tACS frequency stimulation 2, heart rate variability biomarker; F: Guided meditation 4, no stimulation, heart rate variability biomarker and bioimpedance.

The state phase set can consist of the following configurations:

A: Guided meditation 1, tACS, heart rate variability biomarker or bioimpedance; B: Guided meditation 2, high frequency stimulation 1, heart rate variability biomarker; C:

Guided meditation 2, high frequency stimulation 2 stimulation, heart rate variability biomarker; D: Guided meditation 3, high frequency stimulation 1, heart rate variability biomarker or bioimpedance; E: Guided meditation 4, very high tACS frequency stimulation 1, heart rate variability biomarker; F: Guided meditation 4, no stimulation, heart rate variability biomarker or bioimpedance.

The state phase set can consist of the following configurations: A: Guided meditation 1, no stimulation, heart rate variability biomarker; B: Guided meditation 2, magnetic stimulation, heart rate variability biomarker; C: Guided meditation 2, magnetic stimulation 2, heart rate variability biomarker; D: Guided meditation 3, no stimulation, heart rate variability biomarker; E: Guided meditation 4, magnetic stimulation 3, heart rate variability biomarker; F: Guided meditation 4, no stimulation, heart rate variability biomarker.

The state phase set can consist of the following configurations:

A: Guided meditation 1, no stimulation, transimpedance biomarker; B: Guided meditation 2, high frequency stimulation, transimpedance biomarker; C: Guided meditation 2, tACS stimulation, transimpedance biomarker; D: Guided meditation 3, no stimulation, transimpedance biomarker; E: Guided meditation 4, very high tACS frequency stimulation 2, transimpedance biomarker; F: Guided meditation 4, no stimulation, transimpedance biomarker.

Still referring to FIG. 2, the state phase set can consist of the following configurations:

A: Guided meditation 1, no stimulation, transimpedance biomarker; B: Guided meditation 2, high current tDCS stimulation, transimpedance biomarker; C: Guided meditation 2, not stimulation, transimpedance biomarker; D: Guided meditation 3, high current tDCS stimulation, transimpedance biomarker; E: Guided meditation 4, high current tDCS stimulation 2, transimpedance biomarker; F: Guided meditation 4, no stimulation, transimpedance biomarker.

Also, biomarkers can be used to determine when the patient may be at serious adverse event or risk for experiencing undesirable side effects and the state phases 114 are adjusted accordingly. The state phases 114 are adjusted to produce a BTT that avoids hazardous conditions. For example, the intensity of stimulation may be decreased incrementally or to zero. Artificial intelligence, classifiers, signal processing, or machine learning classifiers can be trained on an initial subject set and may be used to determine the stage phases plan for a subject who is not a member of the initial subject set.

Figure 3A:
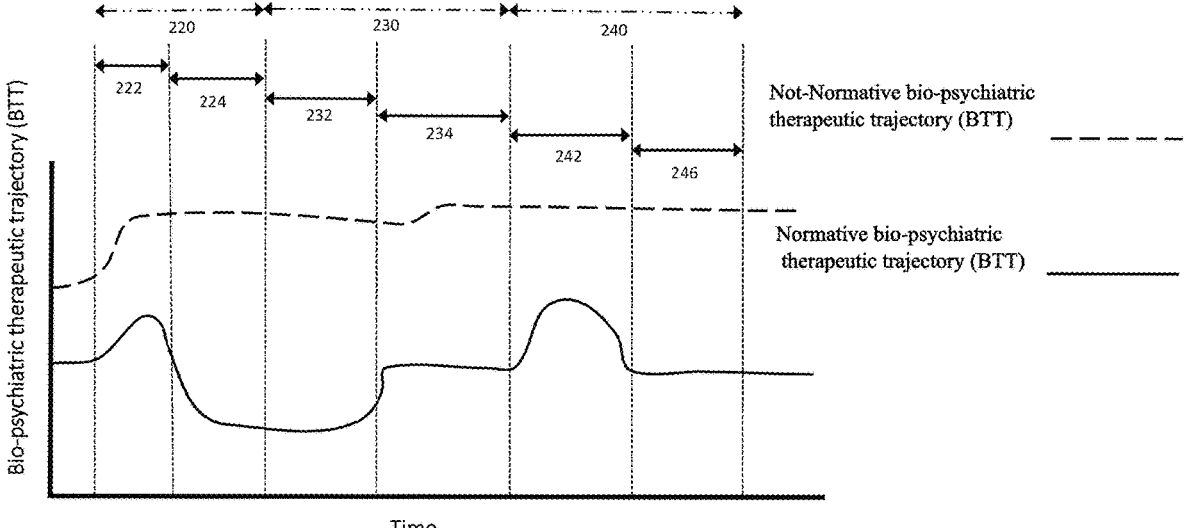
FIG. 3A depicts an example of a normative and a non-normative bio-psychiatric therapeutic trajectory that includes temporal components corresponding to a state phase.

FIG. 3A depicts an example of a normative and a non-normative bio-psychiatric therapeutic trajectory that includes temporal components corresponding to a state phase. The subject bio-psychiatric therapeutic trajectory may be based on a subject mental state, a subject cognitive ability, a subject level of engagement with the engagement component, the engagement component, and the energy application system 130.

The transition path through all the state phases 114 in an engagement component represents a possible bio-psychiatric therapeutic trajectory (BTT). Each BTT may be configured to produce specific changes in physiological state in the subject including a brain state. For example, the BTT may be configured to produce relaxation or command attention. The composition of the BTT includes multiple state phase blocks that combine to form the BTT related to an engagement component.

Still referring to FIG. 3A, the energy emitting device 132 may be configured to modulate the nervous system component 190 so as to alter the physiological changes manifested in the BTT. There is thus two-types of BTTs: an energy absence BTT and an energy present (altered) BTT. For an energy present (altered) BTT, it is sufficient that only a single state phase is altered by the energy application, or some state phases 114 may be altered, or all state phases 114 may be altered.

The BTT may be specific to a subject, change with time, or depend on a disease state. The BTT may be characterize disease states such as depression, cognitive dysfunction, emotional dysfunction, cognitive function, pain, or other indications. The BTT may be a function of subject trait or subject state. The physiological wellness control system 100 may operate a mixed-state-model (MSM). The MSM models trajectories of the BTT based on the subject's conditions specific to the engagement component. A subject with a typical mood following a guided-meditation engagement component is predicted to follow a given BTT. On the other hand, a subject with depression mood following a guided-meditation engagement component is predicted to follow a distinct BTT. The BTT serves as a model of disease state specific to the engagement component.

The signal from the sensor 140 may be processed to diagnose the BTT. A subject with a typical mood following a guided-meditation engagement component may demonstrate specific physiological changes that correspond to a typical mood BTT. A subject with a depressed mood following a guided-meditation engagement component will demonstrate specific physiological changes that correspond to a depression-associated BTT.

Still referring to FIG. 3A, the energy application system 130 may initiate when the engagement component initiates. Energy application may initiate before the engagement component initiates, for example, to prime the brain. Energy application may occur 5 minutes, 10 minutes, or 1 hour before the engagement component primes the brain. Energy application may initiate after the engagement component is initiated. For example, the physiological wellness control system 100 may determine the optimal energy based on the BTT during the initial state-phase block of the engagement component. Energy application may initiate at the start of the second state-phase block.

In one embodiment, a subject with depression is prescribed 30 sessions where each session consists of a unique engagement component, such that there are 30 unique engagement components 112. Each of those 30 unique engagement components 112 is composed of 10 unique state phase blocks. The duration of each state phase block is 1 to 5 minutes. The duration of each engagement component is 5 to 50 minutes. Subjects are instructed to undergo a session daily. Each session is accompanied by energy application using 1, 2, 3, 4, or 5 mA applied for 10, 20, or 30 minutes using at least two electrodes placed on the scalp. Heart rate is monitored during the engagement component either for the entire duration of the engagement component or during the period of the engagement component when energy is applied. Heart rate variability is calculated from the heart rate.

In one embodiment, a subject with cognitive fatigue (or brain fog) is assigned 20 sessions each considering of the same engagement component. The engagement component involves 2 or more state phases 114 (state phase blocks). Energy is applied ramping up 5 minutes before the engagement component, through the entire engagement component, and ramping down for 5 minutes after the engagement component. Performance on the task is recorded by the control system. Performance is used to determine the BTT.

For a high performing (low cognitive fatigue) a BBT is predicted across the state phases 114 and across engagement component. This BTT includes a moderate decrease in performance during an engagement component, indicating normal fatigue. This BTT includes a moderate increase in performance from one engagement component to the next reflecting a normal rate of learning. In an individual with cognitive deficits, performance may start at a lower value and decrease faster during the engagement component. The energy application corrects this deficiency. As a result, this individual with cognitive deficits can show a significant increase in performance from one engagement component to the next. The monitoring of EEG or the monitoring or ECG allow high resolution detection of BTT and more precise energy application updates. When an individual does not show changes in BTT toward the desired target the energy application is updated.

The BTT may be a continuous instant measure or be categorized. One categorization, for example, is 1A, 1B, 2, 3, 4A, 4B. 1A and 1B correspond to strong concordance with the ideal or target BTT. In such cases the energy application and planned engagement components 112 are not changed or changed little. Category 4A and 4B correspond to strong divergence to the ideal or target BTT. In such cases the energy application and/or planned engagement components 112 are changed. Categories 2 and 3 represent states that are close to a desired BTT or close to an undesired BTT, respectively. In category 2, the energy application and planned engagement components 112 are not changed or changed little for an interim period such as one engagement component or one state-block. The BTT is then re-assessed. In category 3, the energy application and planned engagement components 112 are changed incrementally over a limited interim period, such as one engagement component or one state-block. The BTT is then re-assessed. In an alternative embodiment, in category 2 and category 3, one stage phase block is alerted in order to maximize detection of BTT. Analysis of this stage phase block then informs whether stimulation or engagement components 112 are to be changed. A therapeutic treatment plan provided here based on BTT addresses at least some of the shortcomings of prior methods and systems by improving the efficacy of treatment over time.

Still referring to FIG. 3A, the physiological wellness control system 100 can be a closed-loop system and can provide feedback to the subject. The feedback may be in the form of text alerts or interactive tasks. The task or task difficulty may change in response to feedback. The system can provide the subject a diagnosis or diagnostic score. Each engagement component and state phase is programmed as to if and what diagnostic information to display. The diagnostic components can be programmed as modules.

The physiological wellness control system 100 may include a user interface that may be configured to display at least one question. The physiological wellness control system 100 may be configured to determine an electromagnetic dose in response to the at least one question. The engagement component can be used to determine an electromagnetic efficacy in response to the one or more questions.

The BTT represents a time series where the trajectory of the signal provides more information than the instant signal. The BTT trajectory may be a function of the engagement component and its component state phases 114. The BTT trajectory may be based on 1) the subject including the subject's mental state, the subject's cognitive ability, and the subject level of engagement and the 2) engagement component and its component state phases 114*tate* phases and 3) the energy applied by the energy application system 130.

Still referring to FIG. 3A, the physiological wellness control system 100 may be used to treat depression. The engagement component includes at least one guided-meditation task for the subject which involves a sequence of sub-guided meditation activities each a state phase. The engagement component is approximately 40 minutes with 4-10 minutes state phases 114. The BTT depends on attention to guided-meditation in each state phase. Lack of attention or poor attention may result in depressed BTT.

The physiological wellness control system 100 monitors the physiological state. The projected BTT for an ideal or target subject may be predicted over time given the engagement component. The physiological measures are used to calculate the actual BTT. Stimulation is applied if the actual BTT is sufficiently different from the target BTT. Changes in resulting physiological measurements are re-accessed in the context of the current state phase. The energy provided by the stimulator may be increased with increasing deviation of the actual BTT from the desired BTT or may be adjusted according to other known approaches to change stimulation efficacy including changing intensity, pulse width, and/or frequency. The stimulation intensity may increase from 1 mA, to 2 mA, to 3 mA, then to 5 mA until the BTT trajectory is corrected toward a destined state. The stimulation frequency may increase from 1 Hz, to 10 Hz, to 100 Hz, and then to 1000 Hz until the BTT trajectory is corrected toward a destined state. The stimulation location may be more than one target region and may move from one target region to another. If the BTT trajectory is on target to track the ideal or target BTT, stimulation may be maintained at its current level.

Still referring to FIG. 3A, the physiological wellness control system 100 may be configured to measure heart rate using the sensor 140. The sensor 140 may be installed into the headgear attached to the patient. The sensor 140 may be positioned such that a portion of the sensor 140 responsible for the detection of the signal is on the interior surface of the headgear. The sensor 140 may be flush with this interior surface or have no extruding member more than 1 mm inside this interior surface.

Additionally, and/or alternatively, the sensor 140 may be installed on the device such as a hand-held device. In some embodiments, two sensors may be used with one sensor on the head-gear and one sensor on the hand-held device. The sensor 140 on the head-gear may be a light base sensor. The sensor 140 on the hand-held device may be a biopotential-based sensor. A dual pole sensor may be used where one pole is on the hand-held device and one pole is on the head. A dual pole sensor can be a biopotential sensor. The two sensors may be biopotential sensors having at least two electrodes where one electrode is the exterior surface of the hand-held device and one-sensor is on the interior portion of the head gear. The head gear may be made of an elastic or semi-clastic substance. The leads (wires) from the sensor 140 can be embedded in the headgear such that the cable is not evident from the exterior surface.

In some embodiments, the sensor 140 may include a heart rate variability signal feedback monitor system and may be provided for a user or operator by a user interface. The heart rate variability signal feedback monitor system may include a sensor component system sized and configured to be worn or applied to the user by the user. A plurality of electrodes placed in the sensor 140 package may be configured to produce electrical signals based on electrical activity of the user's heart or other signals based on the given measure (such as light). In some embodiments, a vibration output or tactile actuator device affixed to the sensor 140 may be configured to transmit a vibration signal perceptible by the user when the output device is activated. A memory, affixed to housing, stores heart rate variability feedback criteria. The vibration output can be pulsed at 1 Hz to 1000 Hz, and preferably at 1 Hz to 100 Hz. The intensity of vibration output may be calibrated to the individual sensitivity.

In one aspect, the sensor 140 or wearer's electronic module may be connected to the electrodes on the body placed at locations conducive to acquiring heart rate variability. The electrodes can be placed in locations including across the chest, across the arms, or any configuration of locations creating a triangular acquisition configuration. The heart rate variability analysis may then be activated and the heart rate variability analysis processing pipeline may check any connection for either a wired or wireless system, or both. The controller 110 may be configured to collect heart rate variability data from electrodes or sensors placed on the wearer's body (wrist, chest, arm, head, legs). After signal acquisition and showing the heart rate variability data using the heart rate variability analysis pipeline, users or physicians can designate the brain tissues that can be targeted using a desired type of stimulation (e.g., electrical, haptic, light) on the head or on the scalp location.

In one aspect, the controller 110 has a heart rate variability analysis processing pipeline with the capability to store, retrieve, process, and display the wearer's heart rate variability data through the sensor 140. The heart rate variability analysis pipeline may also be able to program and control the energy application system 130 (energy such as electrical, light, haptic) in an electronics module. A high, low or band pass filters may be part of the amplification system in the wearer's electronics module and that they are programmable from commands sent by the heart rate variability analysis pipeline through wired or wireless data connection as well as to a wearer's electronics module.

Still referring to FIG. 3A, the engagement component may include respiratory-driven systems and procedures to provide brain excitation. The respiratory-driven systems and procedures may include at least one energy emitting devices (such as at least one electrode), an energy application system, a user interface, and a method of controlling all aspects of the respiratory-driven system. The respiratory-driven system may be configured to detect the activity of the patient's lung or other respiratory signals in which blood becomes oxygenated and the detected activity of the respiration process is turned into a corresponding detection signal. The detection signal may be configured to be transmitted to the controller 110 that is connected to the analysis and simulation circuit. The controller 110 may be communicatively coupled to the excitation circuit, stimulation circuit, and the detection device, and each may be adjusted to accommodate the incoming respiratory signal. The subsequent stimulation signal may be based on the received detection signal.

In one embodiment heart rate variability may be integrated with a heart rate variable to develop a bio-psychiatric therapeutic trajectory. The bio-psychiatric therapeutic trajectory may be separated into engagement components 112. Each engagement component may include one or more tasks or activity. These tasks may be separated by time into sub-components (state phases 114).

In one aspect, the engagement component may include respiratory-driven systems and procedures to provide brain excitation. The respiratory-driven systems and procedures may include one energy emitting devices (such as at least one electrode), an energy application system, a user interface, and a method of controlling all aspects of the respiratory-driven system. The respiratory-driven system may be configured to detect the activity of the patient's lung or other respiratory signals in which blood becomes oxygenated and the detected activity of the respiration process is turned into a corresponding detection signal. The detection signal may be configured to be transmitted to the controller 110 that is connected to the analysis and simulation circuit. The controller 110 may be communicatively coupled to the excitation circuit, stimulation circuit, and the detection device, and each may be adjusted to accommodate the incoming respiratory signal. The subsequent stimulation signal may be based on the received detection signal.

Still referring to FIG. 3A, the transimpedance circuit may be configured to measure transimpedance that measures the intermediate impedance created by the interaction between the electromagnetic stimulation drive and the body. The transimpedance may be a biomarker that cannot be measured using the neural controlling apparatus alone, in the absence of a body. The transimpedance may be a biomarker that cannot be measured using the body alone, in the absence of an energy application of an electromagnetic device. The transimpedance can represent the complex non-linear impedance of the body load and the associated load produced by the energy application system 130. The transimpedance may be measured by detecting the alteration in the transimpedance circuit or sensor 140 or the energy application system 130 that is a consequence of the transimpedance. The transimpedance representing the interaction between the device and the body may be bridged by the electromagnetic energy. The transimpedance may be a function of the electromagnetic energy. In one embodiment, the electromagnetic energy used for transimpedance coupling matches the impedance provided by the energy application system 130 to change at least one aspect of nervous system function. In this case, the transimpedance circuit of the energy application system 130 is coupled to the electric waveform generator (EWG). In one embodiment, the electromagnetic energy used for transimpedance coupling may not match the impedance provided by the energy application system 130 to change the nervous system function. The transimpedance circuit may include dedicated components.

Transimpedance includes features of the test signal and features of the response signal, which are both coupled inside the transimpedance circuit of the energy application system 130. In one embodiment, the test signal may have one primary feature. This feature may be direct current. The direct current of the test signal may be between 5 uA and 100 mA, preferably at 10 uA to 10 mA, and most preferably at 40 uA to 4 mA. The non-stationary or nonlinear aspects of the body impedance may be coupled with the test signal features to produce the response signal based on the transimpedance circuit of the energy application system 130. In another embodiment, the test signal may have one primary feature and the response signal has two primary features. The two primary signal features may compose of a DC range signal and the remainder in a non-DC range signal. The non-DC range signal may be the AC signal. The DC range signal may be filtered at 0-10 Hz, or preferably at 0-0.1 Hz, or most preferably at 0 Hz. The AC signal may be filtered at 1-10000 Hz, or preferably at 1-1000 Hz, or most preferably at 10-60 Hz.

Still referring to FIG. 3A, the bio-psychiatric therapeutic trajectory may then be derived based on the one feature test signal and a two feature response signal. The test signal may have one, two, three, five or more than five features. The response signal may have one, two, three, five or more than five features. In one embodiment, the test signal may have four features and the response signal has five features. Features of the test signal can include, but are not limited to, any of the output waveforms described here. Features of the test signal can include frequency, intensity, duration, or pulse width. Features of the response signal can include, but are not limited to, any of the signal processing tools described here.

In one embodiment, the transimpedance may be measured every 0.1 to 100 seconds, or preferably every one second to ten seconds, using the sensor 140. Using the sensor 140, the transimpedance may be updated every five seconds to inform the bio-psychiatric therapeutic trajectory. The transimpedance can be coupled to a physical current flow model in the controller 110 software. In one embodiment, the physical current flow model has two free parameters. The two free parameters can be determined based on the transimpedance. When the transimpedance includes two primary signal features, those signal features can inform the two free parameters. The free model parameters can include an aspect of head anatomy such as skull, brain, or skin thickness. The free model parameters can include an aspect of head resistivity such as skull, brain, or skin thickness. In one embodiment, the skin resistivity may be set based on the transimpedance. The current flow models may predict brain current density, brain electric field, power in tissue or other physical outcomes of stimulation. Bio-psychiatric therapeutic trajectory may be updated based on brain current density, brain electric field, power in tissue, or other physical outcomes of stimulation.

Figure 3B:
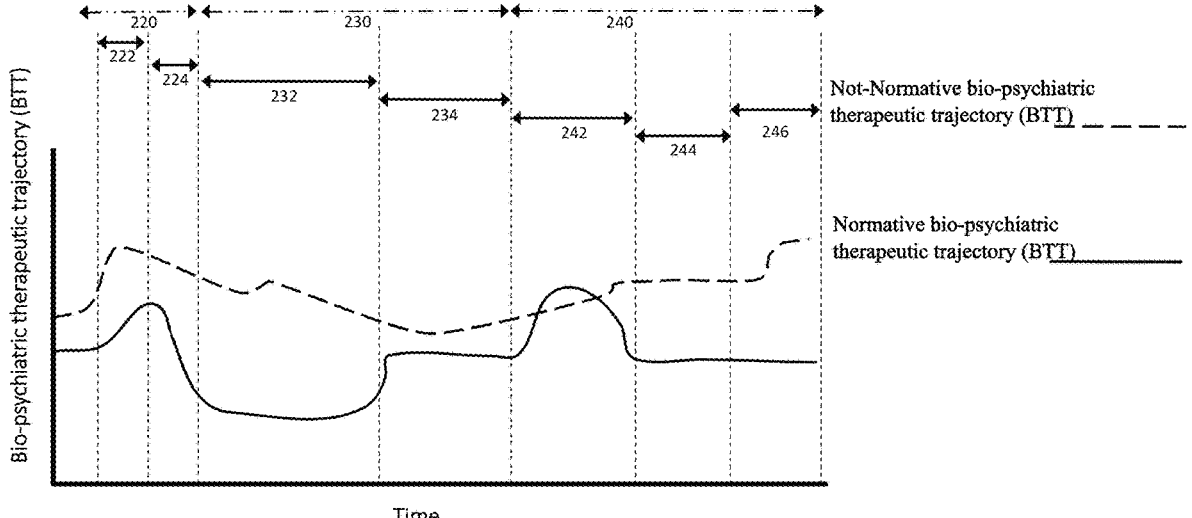
FIG. 3B depicts an example of a normative and a non-normative bio-psychiatric therapeutic trajectory that includes temporal components corresponding to a state phase.

FIG. 3B depicts an example of a normative and a non-normative bio-psychiatric therapeutic trajectory that includes temporal components corresponding to a state phase. The controller 110 may alter the time durations for engagement component 220, engagement component 230, and engagement component 240. The controller 110 may eliminate or adapt the time durations of the correspond state phases. For example, the controller may eliminate stat phase 226 and state phase 236 based on the change in the time duration of the corresponding engagement component. The controller may adapt the time duration of the state phase 222, state phase 224, state phase 232, state phase 234, state phase 242, state phase 244, and state phase 246 based on the change in the time duration of the corresponding engagement component. The subject bio-psychiatric therapeutic trajectory may be based on a subject mental state, a subject cognitive ability, a subject level of engagement with the engagement component, the engagement component, and the energy application system 130.

The controller 110 can update the captured subject bio-psychiatric therapeutic trajectory to determine when a physiological response corresponds to each of the adapted state phases and/or adapted engagement components. The controller 110 can compare the subject bio-psychiatric therapeutic tracking on the adapted state phases and/or adapted engagement components with a normative bio-psychiatric therapeutic trajectory. The controller may select a state phase to move or modify the subject bio-psychiatric therapeutic trajectory in a direction. Additionally the controller may select a second state phase to move or modify the subject bio-psychiatric therapeutic trajectory in a second direction. The normative bio-psychiatric therapeutic trajectory and/or the subject bio-psychiatric therapeutic trajectory may be multi-dimensional. The normative bio-psychiatric therapeutic trajectory and/or the subject bio-psychiatric therapeutic trajectory may extend in a different dimension to represent measurements of a separate variable tracking a bio-marker and or a physiological response.

Figure 3C:
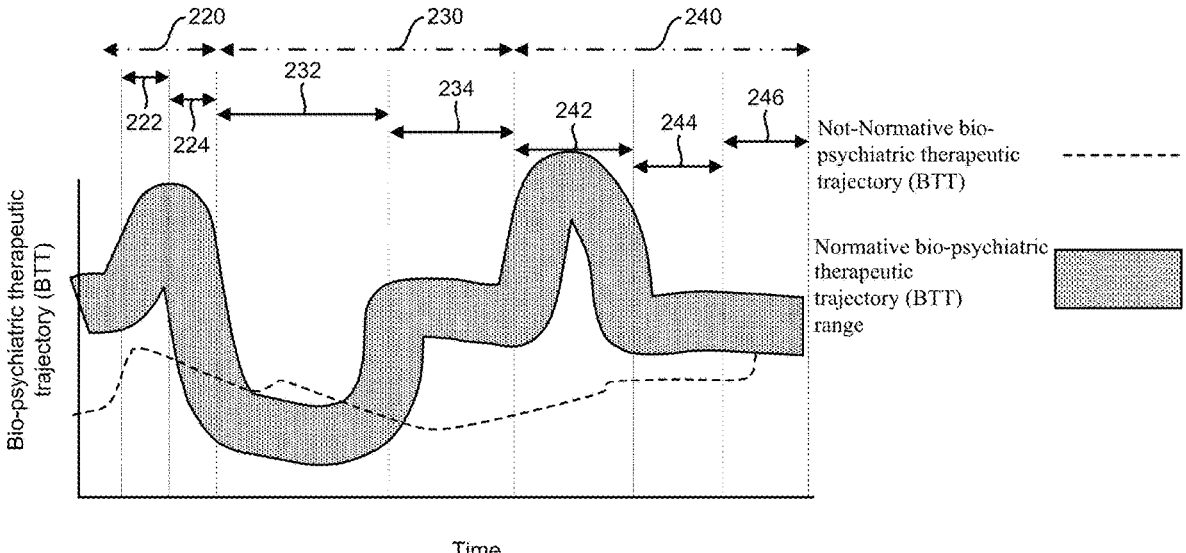
FIG. 3C depicts an example of a normative range and a non-normative bio-psychiatric therapeutic trajectory that includes temporal components corresponding to a state phase.

FIG. 3C depicts an example of a normative range and a non-normative bio-psychiatric therapeutic trajectory that includes temporal components corresponding to a state phase. The normative BTT may encompass a range as shown by the band of possible values for the normative. The state phase transitions may be triggered by the subject BTT entering or exiting this range. The range may be the standard deviation of BTTs collected from the normative populations. The range may be the 99 percent confidence interval of BTTs collected from the normative populations. The range may span the BTT and a multiple of the BTT. In one embodiment, the range is between 0.1× normative BTT and 10× normative BTT. In another embodiment, the range is between 0.5× normative BTT and 2× normative BTT. In another embodiment, the range is between 0.9× normative BTT and 1.1× normative BTT.

The duration of state phases may be controlled. In one embodiment, state phase 222 as the same or approximately the same duration as state phase 224. This duration is preferably 1 second to 60 minutes, or more preferably 10 second 5 minutes. State phase 232 may have a duration longer than state phase 224. The duration of state phase 232 may be 1.5 to 100 times longer than state phase 224. Preferably the duration of state phase 232 is 2 to 20 times longer than state phase 224. State phase 234 may have duration moderately shorter than state phase 232. Preferably state phase 234 has a duration 0.5 to 0.9 of state phase 234. The duration of state phase may be proportional to the deviation of the BTT from the normative BTT. The duration of the state phase may be limited by the time the BTT is within a range of the normative BTT. The transition from one state phase to another state phase may be trigger by a BTT deviation of a prespecified magnitude from the normative BTT. The transition from one state phase to another state phase may be trigger by a BTT deviation of a prespecified magnitude from the normative BTT and a change (slope) of the BTT.

In one embodiment the transition to a new state phase is triggered than the BTT is outside the range of normative BTT for 0.01 to 20 seconds. In a preferred embodiment the transition to a new state phase is triggered than the BTT is outside the range of normative BTT for 1 to 10 seconds.

The state phase set can consist of the following configurations:

A: Cognitive task 1, no stimulation, transimpedance biomarker for 60 seconds. B: Guided meditation 2, Energy stimulation, transimpedance biomarker for 60 seconds. C: Guided meditation 2, Energy stimulation, transimpedance biomarker for 120 seconds. D: Cognitive task 2. no stimulation, transimpedance biomarker for 110 seconds. E: Guided meditation 1, Energy stimulation 2, transimpedance biomarker for 120 seconds. F: Cognitive task 1, no stimulation, transimpedance biomarker for 680 seconds.

The state phase set can consist of the following configurations:

A: Cognitive task 1, no stimulation, transimpedance biomarker for 10 seconds. B: Cognitive task 1, Energy stimulation, transimpedance biomarker for 20 seconds. C: Cognitive task 1, Energy stimulation, transimpedance biomarker for 200 seconds. D: Cognitive task 2, no stimulation, transimpedance biomarker for 10 seconds. E: Cognitive task 2, Energy stimulation, transimpedance biomarker for 100 seconds. F: Cognitive task 1, no stimulation, transimpedance biomarker for 600 seconds.

The state phase set can consist of the following configurations:

A: Energy stimulation Cognitive task 1, transimpedance biomarker for 60 seconds. B: Cognitive task 1, Energy stimulation 2, transimpedance biomarker for 20 seconds. C: Cognitive task 1, Energy stimulation 2, transimpedance biomarker for 200 seconds. D: Cognitive task 2, no stimulation, transimpedance biomarker for 10 seconds. E: Cognitive task 2, Energy stimulation 2, transimpedance biomarker for 100 seconds. F: Cognitive task 1, no stimulation, transimpedance biomarker for 300 seconds.

The state phase set can consist of the following configurations:

A: No energy stimulation, Physical task 1, biomarker for 30 seconds. B: Physical task 1, Energy stimulation 2, biomarker for 320 seconds. C: Physical task 1, Energy stimulation 2, biomarker for 200 seconds. D: Physical task 2, no stimulation, biomarker for 100 seconds. E: Physical task 2, Energy stimulation 2, biomarker for 200 seconds. F: Physical task 2, no stimulation, biomarker for 1200 seconds.

The state phase set can consist of the following configurations:

A: Cognitive task 1, no stimulation, questionnaire, for 120 seconds. B: Guided meditation 2, Energy stimulation, questionnaire for 120 seconds. C: Guided meditation 2, Energy stimulation, questionnaire for 2000 seconds. D: Cognitive task 2, no stimulation, questionnaire for 110 seconds. E: Guided meditation 1, Energy stimulation 2, questionnaire for 120 seconds. F: Cognitive task 1, no stimulation, questionnaire for 2000 seconds.

Figure 4:
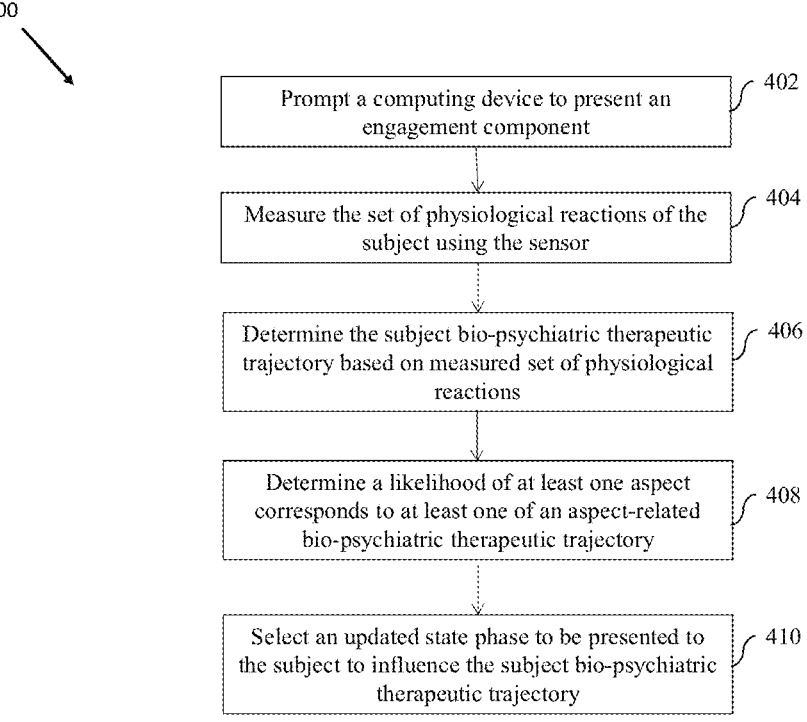
FIG. 4 depicts an example of a flowchart of a method configured to select an updated state phase to be presented to the subject to influence the subject bio-psychiatric therapeutic trajectory.

FIG. 4 depicts an example of a flowchart of a method configured to select an updated state phase to be presented to the subject to influence the subject bio-psychiatric therapeutic trajectory. The physiological wellness control system 100 may select an updated state phase to be presented to the subject to influence the subject bio-psychiatric therapeutic trajectory to match a healthy bio-psychiatric therapeutic trajectory selecting, in response to determining the likelihood of at least one of the physiological state pattern, the cognitive state, the mood, or the disease in the subject. The updated state phase including at least one of an updated cue, an updated biofeedback, or an updated waveform from the energy application system 130 applied to the subject head.

The energy application system 130 may be configured to alter the BTT. The brain wellness control system can predict a desired BTT and used the sensor 140 to detect deviation from the desired BTT. The physiological wellness control system 100 may be configured to stimulate the subject to drive the BTT toward a destined state. For example, the energy from the energy application system 130 may be applied to a depression subject to produce a BTT corresponding to a healthy subject. The BTT and the energy application of energy to the subject are divided by state phases 114.

In some embodiments, the physiological wellness control system 100 can select an engagement component based on subject treatment goals and prior BTT trajectory and measurements. The physiological wellness control system 100 may adjust state phase selection or state phase-phase block order based on BTT trajectory.

The physiological wellness control system 100 may prompt at least one of the user device to present a cue to the subject or the energy application system 130 to apply the electrical stimulation to the subject based on the selected state phase. In response to prompting at least one of a user device to present a cue to the subject or the energy application system 130 to apply the electrical stimulation to the subject based on the selected state phase, physiological wellness control system 100 can measure the set of physiological reactions of the subject using the sensor 140, the set of physiological reactions induced by the selected state phase. The physiological wellness control system 100 can determine a subject bio-psychiatric therapeutic trajectory based on the measured set of physiological reactions from the subject, the subject bio-psychiatric therapeutic trajectory generated by mapping the set of physiological reactions from the subject to the state phase. The bio-psychiatric therapeutic trajectory may be indicative of a physiological state pattern or a cognitive state of the subject. The mapping of the set of physiological reactions from the subject to the state phase may include stitching the temporary components (e.g., state phase blocks) of the physiological reactions, overlapping an intensity of a physiological reaction with a time component received from the sensor 140, transforming the physiological reactions from one mathematical domain to another mathematical domain, and calculating a difference between an expected physiological reaction and an actual anticipated reaction to produce the BTT trajectory. In some embodiments, a machine learning model or an artificial intelligence may map the physiological reactions based on changes in the physiological responses and a learned history of physiological responses.

Still referring to FIG. 4, the set of physiological reactions are at least one of a heart rate spectrum second-order metrics biomarker or a transimpedance biomarker, and wherein at least one physiological reaction of the set of physiological reactions is modulated by the energy application system 130 coupled to the subject.

The updated state phase flowchart 400 may include steps to select an updated state phase. At 402, the controller 110 may prompt a computing device 120 to present an engagement component 112. At 404, the controller 110 may measure the set of physiological reactions of the subject using the sensor 140. At 406, the controller 110 may determine the subject bio-psychiatric therapeutic trajectory based on measured set of physiological reactions. At 408, the controller 110 may determine a likelihood of at least one aspect corresponds to at least one of an aspect-related bio-psychiatric therapeutic trajectory. At 410, the controller 110 may select an updated state phase to be presented to the subject to influence the subject bio-psychiatric therapeutic trajectory.

The physiological wellness control system 100 can be configured to provide a fixed administration schedule to the subject and a fixed measurement schedule to the subject. The physiological wellness control system 100 may be configured to adjust an amount of an electromagnetic dose applied to the subject in response to the BTT data for the subject. The programmed module at the physiological wellness control system 100 can be configured to adjust the schedule of administering the electromagnetic dose of the next engagement component in response to the BTT analysis. In one embodiment, the schedule of sessions in which each session includes at least one engagement component and each engagement component includes at least one state phase, is daily for 5-300 days. In another embodiment, the sessions schedule is daily for 10-60 days. In another embodiment, the sessions schedule is daily for 15-35 days. Sessions may skip days. In one embodiment, a session is provided every other day for 300 days. In some embodiments, a session if provided every other day for 10-60 days. The schedule may be weekly with no sessions being provided on the weekend. In one embodiment, sessions are provided for 2-50 weeks daily except no sessions are provided on the weekend. In some embodiments, sessions are provided for 4-10 weeks daily except no sessions are provided on the weekend. In some embodiments, sessions are provided daily for 5 weeks and then once a week for 5 weeks. In some embodiments, sessions are provided daily for 4 weeks and then once a week for 5 weeks. In some embodiments, sessions are provided daily for 3 weeks and then every other day for 3 weeks. In some embodiments, sessions are provided daily for 3 weeks and then every other day for 5 weeks.

Still referring to FIG. 4, closed-loop neuromodulation is a type of brain machine interface (BMI) that monitors dynamic neuronal and physiological signals to optimize the timing and dosage of brain stimulation, as well as to tailor the stimulation parameters to a particular person. There are optimal and suboptimal times ("windows of opportunity") for stimulation application, which derive from the dynamic nature of inherent physiological states and disease/performance states. Conventional closed-loop approaches: 1) directly monitor disease/performance states (e.g. tremor, fatigue) or decode this from measured signals; 2) compare this current state to a desired target-state, producing and error signal which; 3) gates stimulation based on I/O models (of stimulation biophysics). Success of these approaches depends on the error signal reflecting optimal stimulation times and on stimulation-technology specific I/O models.

A majority of brain stimulation studies remain approaches are open-loop, including most experiments with transcranial electrical stimulation (tES). A preferred closed-loop algorithm—one that encourages development and adoption—would minimize invasiveness and unnecessary stimulation; operate with a time-scale suited to the targeted disease/performance state; and once programmed, would not require tuning with each participant's ground-truth performance. Moreover a broadly scalable and generalizable system would employ data-driven optimization where it can be incrementally trainable from diverse data and any (multiple) stimulation modality (e.g. tDCS, tACS, TMS, tFUS)—essentially allowing for more datasets/modalities, as they become available, to enhance system capabilities.

In one embodiment a framework for designing and implementing closed-loop neuromodulation systems that utilize both deep learning techniques and workflows that avoid explicit state-decoding of stimulation modality (I/O model), and that gates stimulation based on a principle of responsiveness. Responsiveness depends on identifying epochs where a given stimulation modality will increase or improve a defined behavioral or physiological performance outcomes compared to not stimulating. To demonstrate and verify our framework we applied our analysis to the open-source GX dataset with a modified convolutional neural network (CNN; EEGNet} under data-driven optimization. Using provided datasets and a stimulation approach satisfying certain elements, our approach allows scalability and tunability across varied neuromodulation applications.

In one embodiment, the novel closed-loop framework is crafted from several aspects that make up the input (X(t)) to stimulation decision (S(t)) pipeline. These may be grouped into one or more engagement components 112. Input data (X(t)) is passed to a Model Stack, composed of an ensemble of independent models (numbered 1-M), each trained on a unique stimulation condition (in this case No Stimulation, Stimulation Type 1, and Stimulation Type 2. Each ensemble predicts a response (i.e. class labels of an increase or decrease in behavioral or physiological outcomes) per its stimulation condition. These model outputs and confidences are compared under user-defined rules to produce stimulation decisions (Stimulation Decision S(t)). Importantly, the decision is based on responsiveness, namely an improvement in predicted performance with stimulation compared to predicted performance with no stimulation. A final stimulation decision (S(t)) is made where the stimulation type is applied, and the loop continues.

Still referring to FIG. 4, at the point of training, application of this embodiment for data driven closed-loop neuromodulation using machine learning starts with designing an appropriate open-loop stimulation experiment and selecting appropriate deep learning model architectures. The outcomes of these stages serve to verify the feasibility of the given implementation (described below) and ultimately (with additional data collection/training) drive a closed-loop implementation.

The behavioral task used in training sessions in at least one engagement component determines the performance target for the closed-loop system. The stimulation modalities used in training are the options available to the closed-loop intervention, based on biomarkers used within the training data. A simple way to design open-loop trials is with a continuous performance metric within each engagement component, measuring acute changes in performance in response to stimulation, and with biomarkers collected prior to the stimulation (and in the absence of stimulation) to predict responsiveness.

One embodiment does not require that a biomarker predict (decode) performance before or in response to stimulation. Further, whereas conventional closed-loop systems compared decoded brain state/performance against a desired level in order to trigger stimulation; here we require only that the biomarker-derived features indicate a brain state where simulation is likely to improve outcome. For example, detecting sleep in EEG could indicate task performance far from ideal, it would be a useless time to stimulate if the subject remained asleep. In contrast, stimulation responsiveness identifies brain states suggesting both poor performance without stimulation and improved performance with stimulation.

Still referring to FIG. 4, at the point of implementation the input data, denoted as X(t), is provided to the models, and the input data labels (y(t)) are not needed since models are already trained. The input data can consist of a segment of time series data (such as EEG or ECG), sampled at a particular time (t), that should be a biomarker of responsive brain state. There are several model ensembles which form a Model Stack. Each model ensemble is previously trained to precise responses to its designated stimulation type (Stimulation Type 1, Stimulation Type 2 . . . ) and one ensemble trained to identify response to no stimulation (No Stimulation). Within each model ensemble set, each model (models 1-M) can have different architectures or compositions to extract different characteristics of input data, however, all models within an ensemble set should be trained on the same stimulation modality and training data. In one embodiment, the No stimulation model ensemble set can contain multiple convolutional neural network (CNN) models that each have different kernel sizes or different layering architectures.

The main advantage of model stacking embodiment is that it allows for interchangeability and flexibility between ensemble sets within the Model Stack meaning interventions can be added or removed as needed without the need for robust retraining. Interventions can be modified between or during engagement components 112. For example, the Stimulation Type 1 can be completely removed from the system leaving behind only the No Stimulation and Stimulation Type 2 stacks. Similarly a new model ensemble can be added to the Model Stack as needed, to include a new stimulation type. This not only reduces training time but allows for utilizing different cohorts for training data (e.g. varied experiment durations, varied number and rates of stimulation, and both open-loop or closed-loop sessions), provided that their input data type and performance metrics match the Model Stack.

A further aspect of our embodiment involves comparing the outputs from each ensemble of the Model Stack to make a stimulation decision (S(t)). Importantly, this decision is based on the principle of responsiveness which compares the performance predicted with each stimulation type and no stimulation. For example, if the No Stimulation model ensemble predicts that a participant's response will not increase if no stimulation is applied, and the Stimulation Type 1 ensemble set indicates that the participant's response will improve with this type of stimulation, then this indicates responsiveness to Stimulation Type 1 and suggests it should be applied. On the other hand, if the No Stimulation model ensemble predicts that a participant's response will increase with no stimulation applied, and the Stimulation Type 1 ensemble predicts a smaller improvement, then this indicates no responsiveness to Stimulation Type 1 and suggests no stimulation should be applied.

Next, the determination of which stimulation type (S(t)) to apply based on Model Stack outputs, is application specific, and defined by decision rule. One method would be to consider an average or majority vote among each model ensemble set (where predictions are binary outcomes) as well as some metric of confidence with each prediction (e.g. comparing the prediction probability of improvement across all stimulation types, where prediction probabilities are averaged within each ensemble set). The decision rule, as an independent stage, is application specific. For example, if the No Stimulation model ensemble predicts that a participant's response will moderately increase if no stimulation is applied, and the Stimulation Type 1 ensemble set indicates that the participant's response will improve with this type of stimulation, a decision rule may still limit stimulation based on factors like the cost of stimulation (i.e. tolerability, power consumption, elapsed time since last stimulation bout etc.).

Still referring to FIG. 4, when acquiring open-loop data for training a closed-loop algorithm the notion of responsiveness is concerned with identifying biomarker-based features that predict when stimulation is likely to produce an improvement in performance compared to no stimulation. A condition where performance would increase or decrease regardless of if stimulation is applied, can be considered neutral from the perspective of the stimulation value. A condition where performance would increase with stimulation and decrease without stimulation application (i.e. due to vigilance decrements, inattentiveness or sleepiness), is considered positive from the perspective of the stimulation value. A condition where performance would decrease with stimulation and increase without stimulation application, is considered negative from the perspective of the stimulation value. Responsiveness-based gating supports the preferred system feature of minimized unnecessary stimulation ("light touch").

BTT datasets may have multi-modal format (e.g. duration of experiment or number of test stimuli) supporting scalability, and any distinct stimulation modality can be developed in parallel supporting integration. Predicates for our framework is the existence of (and identifying) of at least one fixed stimulation dose that is broadly effective, and the identification of generalized brain states that predicts the time of sensitivity to the ascribed dose—together representing responsiveness. Such features are more likely to exist for interventions with limited focality and where targeted performance is dynamic (on the timescale of mins to sec). In one embodiment, non-invasive approaches is consistent with our suggestion of a preferred platform for scalable training and deployment—such as tES/EEG.

Our framework for closed-loop neuromodulation can be applied to a wide range of applications with use-case specific implementation. One application containing continuous EEG, ECG, EOG and behavioral metrics is in response to low intensity stimulation with varied doses.

Figure 5:
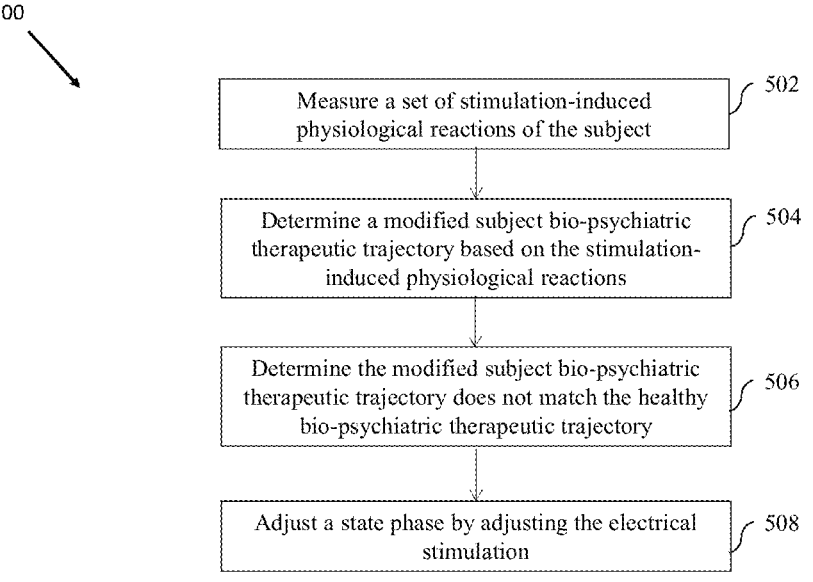
FIG. 5 depicts an example of a flowchart of a method configured to adjust a state phase in response to determining that a modified subject bio-psychiatric therapeutic trajectory does not match a healthy bio-psychiatric therapeutic trajectory.

FIG. 5 depicts a flowchart of a method configured to adjust a state phase in response to determining that a modified subject bio-psychiatric therapeutic trajectory does not match a healthy bio-psychiatric therapeutic trajectory. determining, based on comparing the subject bio-psychiatric therapeutic trajectory to a plurality of historical bio-psychiatric therapeutic trajectories, a likelihood of at least one aspect of the physiological state pattern, the cognitive state, a mood, or a disease in the subject corresponds to at least one of an aspect-related bio-psychiatric therapeutic trajectory or a disease-related bio-psychiatric therapeutic trajectory from the plurality of historical bio-psychiatric therapeutic trajectories, the physiological state pattern, the cognitive state, the mood, or the disease in the subject matching at least one physiological pattern of the aspect-related bio-psychiatric therapeutic trajectory or the disease-related bio-psychiatric therapeutic trajectory.

In one embodiment the protocol for treating cognitive fatigue described above is prescribed to a sufficient number of parents in a first phase. In the first phase, the number of patients can be 10, 100, or 500. In the first phase, the energy applied and the engagement component is fixed. Patient symptoms are accessed through clinical symptom assessment and questionnaires. Patients in the first phase are designated as responders or non-responders based on the change in their clinical presentation. Based on the measured BTT of all subjects, a BTT for responses is determined and a BTT for non-responders is determined. A distinction between BTT is calculated specifically for the first or first few sessions. In the next phase, patients begin the treatment course and their BTT is analyzed in the first or first few sessions. In the next phase, patients whose BTT corresponds to the BTT in the first-phase responder group are predicted to respond clinically. In this patient the energy application and engagement component is not changed. In the next phase, patients whose BTT corresponds to the BTT in the first-phase non-responder group are predicted to not respond clinically. In this patient the energy application and engagement component is changed. Specifically the energy or engagement component is adjusted to produce BTT aligned with responders. In this cohort, after the energy or engagement component is adjusted the BTT is again compared to the performance of responders and non-responders in the first phase. In the next phase clinical symptoms are also collected before and after the treatment course. This data is combined with data from the first phase to further refine BTTs for responders and nonresponders.

Still referring to FIG. 5, an ideal BTT, or several desired BTTs are predicted across each engagement component and across its component state phase blocks. The ideal or desired BTTs are associated with expected changes in heart rate and/or heart rate variability. Subjects undergoing the treatment course whose BTT corresponds to the ideal or desired BTTs are considered responders. Otherwise, subjects are considered non-responders. The energy applied to responders is maintained at the initial settings. The energy applied to non-responders is adjusted from the initial settings. The adjustment applied to non-responders may include operating technique for high current as described here. The current may specifically be increased from 0.1 to 10 mA in steps of 0.1 to 1 mA. In one embodiment, the current is initialized at 2 mA and steps to 4 mA and then to 6 mA. The time point to adjust stimulation settings may come between engagement components 112 such that the data from one engagement component is analyzed and used to decide the stimulation in the next engagement component. The time point to adjust stimulation settings may come between blocks such that the data from one block is analyzed and used to decide the stimulation in the next block component. The analysis may be conducted over several blocks with an engagement component.

Based on data from prior subjections, BTT can be determined using standard "best fit" curve fitting procedures understood in the mathematical arts, and approximated by the mathematical expressions. The equations or mathematical expressions represented by curves can then be used as a standard value for the normal BTT given an energy application. These equations can then be computed for comparison to the incoming data of new subjects as discussed. This reduces the storage and retrieval of numbers of data points which otherwise make up a curve. This also allows faster and more precise synchronization of the standard BTT values with a variety of BTT stimulation periods or sampling intervals across engagement components 112. At least some of the shortcomings of the prior methods may be overcome by use of the BTT.

Still referring to FIG. 5, the adjusted electrical stimulation flowchart 500 may be configured to adjust a state phase 114 by adjusting the electrical stimulation. At 502, the controller 110 may measure a set of stimulation-induced physiological reactions of the subject. At 504, the controller 110 may determine a modified subject bio-psychiatric therapeutic trajectory based on the stimulation-induced physiological reactions. At 506, the controller 110 may determine the modified subject bio-psychiatric therapeutic trajectory does not match the healthy bio-psychiatric therapeutic trajectory. At 508, the controller 110 may adjust a state phase by adjusting the electrical stimulation.

In one embodiment BTT biomarkers of response consisted of 32-channel pre-stimulation EEG and ECG, and labels of response included a behavioral compensatory tracking task (CTT) where participants' goal was to use a trackball to keep a dynamic cursor-controlled circle at the center of the screen at all times. Lower radial ball deviation from the center of the screen indicated good task performance. Stimulation conditions included 9 different combinations of stimulation location (Frontal, Motor, Parietal) and frequency (0, 5, 30 Hz), denoted with the first letter of the location and the frequency number (i.e., Frontal stimulation at 30 Hz as F30). In acquiring the BTT dataset, Experiment 1 was used as a parameter space exploration to identify stimulation conditions that produced the largest degree of behavioral improvement and demonstrate an open-loop effect. Experiment 1 served an important function in framework implementation since a detectable open-loop effect is a prerequisite. Frontal (F30) and Motor (M30) stimulation at 2 mA and 30 Hz, were selected from Experiment 1 and reimplemented in Experiment 2 with more trials and a different cohort.

Once an open-loop stimulation effect on performance is established, models are trained to predict when stimulation would most effectively change performance. In one embodiment, we utilized the data acquired during Experiment 2 as our input training data since we could effectively extract response from individual trials where segments of no stimulation (or pre stimulation) preceded segments of stimulation. We utilized the percent change in average task cursor deviation ($\Delta$) or distance from the center of the screen at each screen frame (~16 Hz), from pre to during stimulation as our response label trial-wise and participant-wise results) and the pre-stimulation EEG and ECG (15 channels×3000 samples) as our predictive brain states to train each of the individual models. For our no stimulation comparisons, data where no stimulation was applied was divided similarly to that of the stimulation portions of data (from 0-20 mins). Each pre-stimulation trial was labeled as Better or Worse, where class labels were binned identifiers calculated from the percent change in behavioral performance (CTT deviation) during stimulation compared to the pre-stimulation period. A negative percent change in deviation (~$\Delta$, compared to pre stimulation) was classed as Better, whereas a positive change in deviation (+$\Delta$, compared to pre stimulation) was classed as Worse. In terms of model architecture, a modified CNN (EEGNet architecture) was used with differing input kernel lengths/

Still referring to FIG. 5, the BTT dataset was used to present and verify a proof-of-concept of the application of our framework across engagement components 112. Data from an experiment, met our framework criteria (for training data) of an open-loop effect of stimulation and CNN models were selected to be applied to the dataset. For our framework verification and proof-of-concept, data an experiment were selected for further analysis in order to maintain homogeneity with experimental intervention timing and maximize the number of training trials.

For each stimulation condition (No Stimulation, F30, M30) two models, each with differing kernel lengths were tasked with producing binary classifications of trials of pre-stimulation input data (14 EEG and 1 ECG channels× 3000 samples). Each of the 6 models produced prediction accuracies of trial-wise binarized change in deviation (Better: a CTT deviation less than pre stimulation period, Worse: a CTT deviation more than pre stimulation period) above 50%, indicating that models were able to effectively ingest minimally processed input data (EEG and ECG) and that the input data across stimulation conditions contained predictive information on responsiveness. Models 1 and 2, for the No Stimulation condition reached respective cohort testing (816 total trials; Better/Worse ratio: 1.0503) accuracy of 73.5% and 73.2%, and misclassifications of 26.5% and 26.8%. Similarly for the F30, both Models 1 and 2 reached cohort testing (120 total trials; Better/Worse ratio: 2.6364) accuracy of 67.5%, and misclassifications of 32.5%. For M30, Models 1 and 2 reached respective cohort testing (120 total trials; Better/Worse ratio: 3.2857) accuracy of 71.7%, and 69.2%, and misclassifications of 28.3% and 30.8%.

Due to the open-loop effect of stimulation across stimulation conditions, training and testing data suffered from class imbalances between both classes (Better and Worse). Weighted (by class frequency) metrics of precision, recall, and F1 were therefore calculated to better reflect model performances. Aforementioned metrics along with the area under the precision-recall curves (PR-AUC) were computed as the mean and standard error of the mean (SEM) across participants and trials (N=6, Stim: 20 and NoStim: 136 trials for each participant) in the test set. Transimpedance measures provide further data sets for restricting outputs.

Model accuracy scores were 75.4±1.0% (Model 1) and 73.2±1.0% (Model 2) for No Stimulation; 67.5±5.7%

(Model 1) and 67.5±5.7% (Model 2) for F30; and 71.7±9.4% (Model 1) and 69.2±8.5% (Model 2) for M30. Model F1 scores were 75.2±1.1% (Model 1) and 73.2±1.0% (Model 2) for No Stimulation; 64.9±6.2% (Model 1) and 65.6±5.7% (Model 2) for F30; and 72.1±9.3% (Model 1) and 70.0±8.5% (Model 2) for M30. Precision scores were 73.6±3.7% (Model 1) and 72.8±2.2% (Model 2) for No Stimulation; 60.9±8.8% (Model 1) and 63.7±7.8% (Model 2) for F30; and 76.9±12.1% (Model 1) and 77.1±11.9% (Model 2) for M30. Recall scores were 78.3±3.1% (Model 1) and 73.9±1.6% (Model 2) for No Stimulation; 76.1±6.5% (Model 1) and 74.2±7.6% (Model 2) for F30; and 72.0±7.1% (Model 1) and 70.4±7.0% (Model 2) for M30. PR-AUC scores were 0.84±0.03 (Model 1) and 0.82±0.02 (Model 2) for No Stimulation; 0.66±0.15 (Model 1) and 0.66±0.19 (Model 2) for F30; and 0.78±0.29 (Model 1) and 0.78±0.29 (Model 2) for M30.

Predictions for the No Stimulation condition had a relatively balanced correct classification between both classes and correct classifications were widely distributed over percent changes in deviation. For F30 and M30 stimulation conditions, correct predictions were skewed to the major class (Better), where a higher percentage of the major class was correctly predicted as compared to the minor class (Worse).

These results indicate that models within ensemble sets (e.g. Model 1 and Model 2 would be an ensemble for No Stimulation) for all stimulation conditions utilized, can effectively identify out-of-training responsive trials. These predictions (for each stimulation type) can then be compared directly post-prediction to determine the appropriate stimulation decision and stimulation application of each trial.

Still referring to FIG. 5, once trained all models can then be combined to produce responsiveness predictions. To demonstrate responsiveness predictions, comparisons, and stimulation decision making; all test trials were individually passed as inputs to an ensemble of all 6 models. Model predictions were aggregated and averaged and responsiveness comparisons were made followed by a simple decision rule, where the maximum probability of improvement across stimulation intervention types (above a threshold of 0.65) was selected as the stimulation decision. The responsiveness comparisons and stimulation decisions for 10 exemplary trials. In terms of the responsiveness comparisons with our implementation, a decision rule algorithm first considers if the average NoStim probability of improvement is more than 0.65. If yes then the stimulation decision is NoStim, if not then F30 and M30 are compared directly to check that both their probabilities of improvement are more than 0.65 and that one average probability is more than the other, leading the either F30 or M30 being chosen as the stimulation decision. If these criteria are not met the stimulation decision reverts to NoStim, inline with our "light touch" approach to stimulation.

To assess the responsiveness predictions, stimulation decisions were classified into correct assessments, potential improvements, wrong assessments, or missed opportunities. This was done for each test set data type as well as all test set trials. Trials classed as correct assessments were instances where the stimulation decision matched the label of the given stimulation intervention that was applied and showed an improvement in behavioral performance. Potential improvements indicated trials where the stimulation decision was an intervention type that could have resulted in a behavioral improvement based on open-loop effects. Wrong assessments were trials where the stimulation decision was an intervention that was known to produce a given decrement in behavioral performance, given trial labels. Missed opportunities were trials where the stimulation decision was to apply no stimulation, even though trial labels indicated that there would be behavioral improvements with a given intervention type (i.e. F30 or M30). The process thus follows a first stage and second stage.

In one embodiment, a novel theoretical framework for implementing data-driven closed-loop stimulation that is scalable in terms of stimulation modalities and training datasets; agnostic to stimulation modalities being applied; and omits the need for ground truth performance data in its application stage. Leveraging as base NIBS training data and deep learning techniques, we demonstrate a proof-of-concept. We show that with this structured technique, minimally processed neural and physiological input data can be used to effectively identify conditions anticipating stimulation responsiveness. In a closed-loop system, these identified states of responsiveness can then be used to predict when and which stimulation will provide performance benefit.

One embodiment leverages tools from prior closed-loop techniques but provides special benefits in overall implementation. Agnosticism to modality allows any stimulation modality (e.g. electrical, ultrasound) to be incorporated provided open-loop training data. As such we avoid an explicit I/O model (hypothesized mechanism). One embodiment also parallelizes stimulation predictions across modalities allowing integration into a single controller. The expandable training stage is distinct from closed-loop implementation, omitting the need for ground truth performance in the target participant. Together these support scalability. One embodiment hinges on selecting a time-scale for prediction, that would be informed by time-course of the stimulation and performance change. The time scale may be 0.01 to 100 second, or preferably 1 to 10 seconds.

Still referring to FIG. 5, one embodiment revolves around the concept of responsiveness. This circumvents the reliance of closed-loop systems to decode a hidden brain state (performance) to compare a target condition, with the resulting error triggering stimulation (based on a separate I/O model). Rather, responsiveness predicts how a given stimulation modality will change performance, which can be compared to expected performance without stimulation (or with another stimulation modality). Transimpedance may be used as the primary biomarker. Application-specific decision rules can then be implemented within or across engagement components 112. for example based on the confidence of prediction or the costs of stimulation. Once fully defined, all aspects of this embodiment can be implemented to make autonomous stimulation decisions yielded enhanced outcomes. Responsiveness is thus a feature of BTT.

Figure 6:
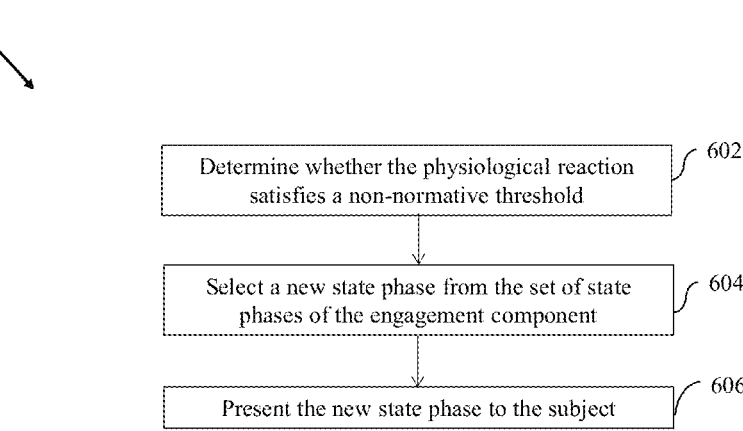
FIG. 6 depicts an example of a flowchart of a method configured to select a new state phase form the set of state phases of the engagement component.

While this embodiment can be applied to any recording and stimulation approaches, the reliance on non-invasive and tolerated modalities reduces barriers to use, including for wellness and performance applications. The analysis and implementation here with the BTT datasets is exemplary in that it serves as a demonstration of our proposed framework and aids in validating our approach. With additional experimental datasets and techniques like generative modeling for producing larger training sets, the performance of this embodiment becomes expandable with potential increases in predictive performance Referring to FIG. 6, illustrated is a flowchart of a method configured to select a new state phase form the set of state phases 114 of the engagement component. The controller 110 may determine the non-normative threshold being indicative of an expected physiological reaction of subjects reacting to the state phase based on a plurality of historical bio-psychiatric therapeutic trajectories in response to presenting the state phase to the subject, whether the physiological reaction reactive to the state phase satisfies a non-normative threshold. The controller 110 may select a new state phase from the set of state phases 114 of the engagement component, the new state phase not predetermined to be presented as a next state phase after the state phase in response to the physiological reaction reactive to the state phase satisfying the non-normative threshold. The controller 110 may prompt at least one of the user device to present the new cue, the user device to present the new biofeedback, or the energy application system 130 to apply the new waveform based on the new state phase.

The controller 110 may prompt the energy application system 130 to apply the electrical stimulation with a modality of at least one of a tDCS, tACS, TMS, or tFUS current to the subject head, the at least one of a tDCS, tACS, TMS, or tFUS current proven to adjust at least one of heart rate spectrum second-order metrics or a transimpedance across the first energy-emitting device and the second energy-emitting device coupled to the subject head. The non-normative flowchart 600 may be configured to present the new state phase to the subject in response to the physiological reaction satisfying a non-normative threshold. At 602, the controller 110 may determine whether the physiological reaction satisfies a non-normative threshold. At 604, the controller 110 may select a new state phase from the set of state phases of the engagement component. The controller 110 may present the new state phase to the subject.

Still referring to FIG. 6, the energy application system 130 may apply an optimized energy frequency. This can include tACS. The stimulation frequency is selected from frequencies known to modulate targeted neuronal activity including oscillations. The targeted oscillations are in the range of 0.1-1000 Hz, or 1-100 Hz, or 2-40 Hz. A conventional frequency range for neuromodulation is in the range of 0 to 100 Hertz or more broadly 0 to 1000 Hz, or still more broadly 0 to 20,000 Hz. Therefore, for the present method, frequencies within this range are employed for neuromodulation. The initial stimulation frequency set for the first engagement component and the first phase block is selected anywhere within the chosen range and depends on the type of neural element, structure or activity being targeted. The initial frequency is preferably set to begin stimulation near where the maximum response of this target is expected. The change in frequency over time, including the selection of the first frequency, is guided by the BTT.

After the necessary circuits, support materials, amplifiers and control equipment has been assembled and programmed, including the control system and sensors, the system is tested, energy sources such as electrodes are connected between the stimulator outputs (electric waveform generator: EWG) and the target region of the nervous system. The system configuration is based on the set of BTT expected across the patient group in which the system will be used.

Once the first frequency is selected and the system adjusted to produce an energy output at that frequency, stimulation energy is delivered to the targeted nervous system as the prescribed time based on the engagement component. In one embodiment the stimulation has a duty cycle. The duty cycle can range from 5% to 100%. Stimulation can be on for 2 seconds after which no stimulation is provided for a period of 5 to 15 seconds. Stimulation can be on for 10 seconds after which no stimulation is provided for a period of 5 to 15 seconds. Stimulation can be on for 1 seconds after which no stimulation is provided for a period of 1 to 10 seconds. Stimulation can be on for 0.1 seconds after which no stimulation is provided for a period of 0.1 to 2 seconds. Stimulation can be on for 0.01 seconds after which no stimulation is provided for a period of 0.1 to 1 second. This allows the neuronal target to recover between stimulation on periods and well as engaging with neuronal systems that naturally respond to such inputs.

Still referring to FIG. 6, during stimulation the targeted neuronal elements are engaged by the engagement component. Depending on the presentation to the subject such as audio or video and depending on the prompts to the subject such as engaging in task brain regions will be activated in a spatial and temporal specific manner. For tasks activating frontal brain regions such as the prefrontal cortex or the DLPFC, energy is applied to the frontal cortex. The engagement component, and specifically the brain-state phases 114, are configured to produce change in brain state during the course of the session. In one embodiment the stimulation energy is adjusted alongside this predicted change in brain state. A subject is prompted to execute a task activating a first brain region and energy is applied to the first brain region. The subject is prompted to execute a task activating a second brain region and energy is applied to the second brain region. In one embodiment the sequence of engagement components 112 may be configured to produce a sequence of brain activity changes and energy is adjusted accordingly. In one preferred embodiment, over at least three engagement components 112 the level of brain activity prompted if gradually increased. Stimulation energy is increased proportionally. The following pattern of brain activity and energy are preferable across engagement components 112: 1, 1.5, 3. The following pattern of brain activity and energy are also preferable across engagement components 112: 1, 5, 6. Each of these patterns, when matched by energy application, can optimize stimulation outcome.

Sensors serve as biomarker informing BTT. The same or additional sensors can be applied to confirm performance in a task such as a motor task monitored with EMG. This allows monitoring of when muscles relax and recover, as for example from the exercise as is done for most rehabilitation protocols. The work being performed or torque exerted through the muscles by contraction is measured and recorded. The engagement component includes a schedule of when muscle activation is expected and/or the type of muscle patterns. Analysis of EMG activity and comparison with the engagement component by the control allows documentation of compliance or effort. Analysis of transimpedance and comparison with the engagement component by the control allows documentation of compliance or effort. Under conditions of inadequate compliance or effort the system may adjust the following stimulation phase block task, instructions, or energy pattern. The EMG is also factored in the BTT for example in rehabilitation there is a target BTT state that includes physical performance. The transimpedance is also factored in the BTT. The system may also suspect of stop the engagement component if performance falls out of range.

Still referring to FIG. 6, EMG activity or a signal processed from EMG, or other physical measures such a torque may be displayed to the operator. The display is part of the engagement component display system. In one embodiment the display is part of the user interface. The information may be displayed in a number or in a graphical format such as a dual or colored meter. EEG activity, EKG activity, or other physiological measures can be displayed to the subject in raw or processed form. BTL can display the subject. Any current reading can be compared to a target level. In this way the subject is provided biofeedback. The target level varies with the engagement component. In one embodiment, the first state phase of an engagement component provides an indication to lower heart rate variability (heart rate variability) and the second state phase of the engagement component provides an indication to modestly increase heart rate variability. The prompted changes are relative based on recording prior to the initiation of the engagement component. The target values can therefore be expressed as a ratio of the initial value. For the heart rate variability example mentioned above the preferred pattern is 0.9 and 1.1.

Another preferred pattern is 0.8 and 1.2. This pattern may be repeated in extended blocks of the engagement component. For example 0.9, 1.1, 0.9, 1.1, 0.9, 1.1. The stimulation energy may be adjusted proportionally to the heart rate variability target. In one embodiment the stimulation across state blocks within an engagement component is 1.8 mA, 2.2 mA, 1.8 mA, 2.2 mA, 1.8 mA. 2.2 mA. In one embodiment the stimulation across state blocks within an engagement component is 2 mA, 3 mA, 2 mA, 3 mA, 3 mA, 3 mA. In one embodiment the stimulation across state blocks within an engagement component is 3 mA, 2 mA, 2.5 mA, 3 mA, 2 mA, 3 mA. In one embodiment the stimulation across state blocks within an engagement component is 3 mA, 4 mA, 2 mA, 3 mA, 2 mA, 3 mA. In one embodiment the stimulation across state blocks within an engagement component is 2 mA, 3 mA, 4 mA, 3 mA, 2 mA. In a further embodiment the displayed heart rate variability is adjusted based on the performance of the subject.

When the engagement component includes a rehabilitation component a conventional treatment protocol exercises a muscle for no more than about 20 minutes to avoid excessive fatigue and injury. A second engagement component can increase stimulation to 30 minutes. A third engagement component can increase stimulation to 40 minutes. This integration provides an incremental increase of the amount of work performed by the muscles during an engagement. During the course of the engagement component if performance is found to decrease, for example based on EMG, the stimulation energy may be increased. In one embodiment, for every 10% decrease in performance stimulation is increased by 1 mA. In one embodiment, for every 5% decrease in performance stimulation is increased by 1 mA. In one embodiment, for every 10% decrease in performance stimulation is increased by 0.5 mA.

The impact of energy frequency coupled to the neuronal targets is varied. An alternative method of varying the energy to the neuronal targets is to vary the pulse width of the stimulation signals. Instead of adjusting the frequency in steps during the engagement component, the pulse width is adjusted in steps during the engagement component, or across engagement components 112. The adjustment or steps may be predetermined and/or based on deviation from the BTT. In one embodiment the frequency and pulse width are varied so as to maintain stimulation energy.

Still referring to FIG. 6, the embodiments provide a closed loop brain electric stimulation device and a method for making it, which increases the accuracy of brain electrical signal processing and the performance of brain electrical stimulation. The embodiments may incorporate a brainwave receiving system, a processor, and a stimulation power generator in a closed-loop brainwave stimulation device. A variety of brain electrical impulses are obtained by the brain wave receiving device. The controller 110 is connected to the brain wave receiving device and performs computational, brain wave specific operations on the EEG signals over a number of time intervals to obtain a number of operation resultant values, whereby it generates a stimulation waveform or activation signal predicated on each of the previous procedural steps values.

In one embodiment, when the value of each computational operation reaches a predefined threshold for the computational operation, the controller 110 provides a stimulus activation signal or stimulation waveform. In one embodiment, the controller 110 may be configured to set a preset critical phase or computational operation value based on a plurality of reference data. The reference data is stored in the memory device, which is connected to the controller 110.

The controller 110 of one embodiment also involves calculating a number of EEG signal energy spectral densities at successive time intervals and producing a stimulation start signal based on each energy spectral density and the corresponding phase operation value.

In one embodiment, when the controller 110 determines that each energy spectral density is not less than a preset critical energy value and the absolute value of the corresponding phase operation value is not less than a preset critical phase value, the controller 110 generates a stimulus activation signal.

A communication unit may be included in the physiological wellness control system 100. The communication unit is connected to the controller 110, and it is through the communication unit that the controller 110 communicates with the external host. Receiving a multitude of EEG signals; performing computational operations on the EEG signals in successive time intervals to obtain a multitude of resultant computational operation values, and each computed value calculated can generate a stimulus activation signal or stimulation waveform; and, based on the stimulation initiation signal, to generate a stimulation voltage or current.

Figure 7:
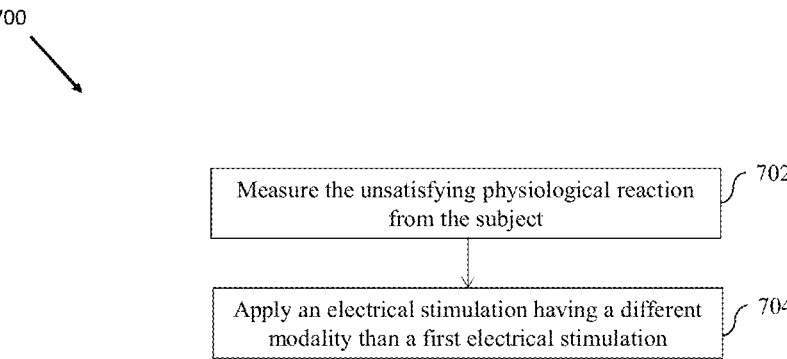
FIG. 7 depicts an example of a flowchart of a method configured to apply an electrical stimulation having a different modality than a first electrical stimulation.

Referring to FIG. 7, illustrated is a flowchart of a method configured to apply an electrical stimulation having a different modality than a first electrical stimulation. The physiological wellness control system 100 may measuring a set of stimulation-induced physiological reactions from the subject using the sensor 140 in response to prompting at least one of the user device to present the updated cue, the user device to present the updated biofeedback, or the energy application system 130 to apply the updated waveform based on the updated state phase. The physiological wellness control system 100 may determine a modified subject bio-psychiatric therapeutic trajectory based on the stimulation-induced physiological reactions from the subject. The physiological wellness control system 100 may determine the modified subject bio-psychiatric therapeutic trajectory does not match the healthy bio-psychiatric therapeutic trajectory. The physiological wellness control system 100 may adjust the updated state phase to make the subject bio-psychiatric therapeutic trajectory match the healthy bio-psychiatric therapeutic trajectory by adjusting the electrical stimulation to the subject head in response to determining the modified subject bio-psychiatric therapeutic trajectory does not match the healthy bio-psychiatric therapeutic trajectory. At least one of an intensity, a pulse width, a time applied, or a frequency of the adjusted electrical stimulation is different from the first electrical stimulation.

The controller 110 may prompt the energy application system 130 to apply the electrical stimulation with a modality of at least one of a tDCS, tACS, TMS, or tFUS current to the subject head, the at least one of a tDCS, tACS, TMS, or tFUS current proven to adjust at least one of heart rate spectrum second-order metrics or a transimpedance across the first energy-emitting device and the second energy-emitting device coupled to the subject head.

The modality can include at least one of tACS and a frequency. The frequency of tACS may be a linear function of the error. In a further embodiment the frequency of tACS is a linear function of the error bounded by a minimum tACS frequency and maximum tACS frequency. The minimum tACS frequency may be 1 or 2 or 10 Hz. The maximum tACS frequency may be 1 kHz, or 10 kHz, or 20 kHz, or 100 kHz. High frequency tACS may be the upper bound as described. The bounding may change from one state phase to another state phase. In one embodiment the maximum tACS frequency bounding is 2 kHz and in a later state page the maximum tACS current frequency bounding is 10 kHz or 40 kHz. The transition of maximum tACS bounding frequency can be guided by answers provided by the subject or biomarkers. In a preferred embodiment these biomarkers are heart rate, impedance, heart rate variability or transimpedance.

Still referring to FIG. 7, the controller 110 may measure, in response to prompting the energy application system 130 to apply the electrical stimulation to the subject head, an unsatisfying physiological reaction from the subject using the sensor 140. The unsatisfying physiological reaction may be induced by the energy application system 130 coupled to the subject head. The unsatisfying physiological reaction failing to satisfy a healthy physiological reaction threshold indicative of a healthy physiological reaction by a healthy individual. The different modality flowchart 700 may enable an application of an electrical stimulation having a different modality. At 702, the controller 110 may measure the unsatisfying physiological reaction from the subject. At 704, the controller 110 may apply an electrical stimulation having a different modality than a first electrical stimulation.

The controller 110 may prompt the energy application system 130 to apply a second electrical stimulation from the energy application system 130 at the next state phase in the set of state phases 114 of the engagement component in response to measuring the unsatisfying physiological reaction from the subject using the sensor 140. The second electrical stimulation may be applied to the subject head. The second electrical stimulation may have a different modality from the at least one of a tDCS, tACS, TMS, or tFUS current.

The modality can include at least one of tES (including (DCS), TMS, ECT, ultrasound, photobiomodulation, light-based, and/or the like. Energy sources may be selected from tES (including (DCS), TMS, ECT, ultrasound, photobiomodulation or light-based, etc. Specifically, for tDCS, intensities range from 1-5 mA, and preferably 5 mA, and the time course is 10-30 min per session. The session can be divided into engagement components 112. In one embodiment, tDCS is provided under a high current mode which is directed toward an engagement component selected by on an initial assessment (the first stage in a two stage process).

Still referring to FIG. 7, the modality can include at least one of a high current mode and a low current mode. The high current mode includes at least one component of tDCS with a current of 4-20 mA, preferably 4-10 mA. At least one state phase of at least one engagement component includes a high current. The application of high current produces an alteration in BTT trajectory such as to normalize response in selected subjects. In a preferred embodiment the state phase with high current is part of a sequence of state phases 114 (which can be indexed as a, b, c, d, e, f . . . ). The sequence of state phases 114 overcomes at least some limitations in the prior art by allowing high current tDCS to be applied in an individualized manner.

The prescribed sequence of state phases 114 can be: a) No electromagnetic output. Task or instruction set 1; b) tDCS output that is not high current Task or instruction set 1. Biomarker 1; c) (DCS output at high current. Task or instruction set 2. Biomarker 2; d) No electromagnetic output. Instruction set 2.

The prescribed sequence of state phases can be: a) No electromagnetic output. Task or instruction set 1; b) tDCS output is high current Task or instruction set 1. Biomarker 1; c) tDCS output at high current. Task or instruction set 2. Biomarker 2; d) no electromagnetic output. Instruction set 2.

The prescribed sequence of state phases can be: a) No electromagnetic output. Task or instruction set 1; b) tDCS output that is not high current Task or instruction set 2. Biomarker 1; c) tDCS output at high current. Task or instruction set 2. Biomarker 1; d) No electromagnetic output. Instruction set 2.

The prescribed sequence of state phases can be: a) No electromagnetic output. Task or instruction set 1; b) tDCS output that is not high current Task or instruction set 2. Biomarker 1; c) tDCS output at high current. Task or instruction set 2. Biomarker 2; d) tDCS output that is not high current Task or instruction set 3. Biomarker 2; e) no electromagnetic output. Instruction set 4.

The prescribed sequence of state phases can be: a) no electromagnetic output. Task or instruction set 1; b) tDCS output that is not high current Task or instruction set 2. Biomarker 1; c) tDCS output at high current. Task or instruction set 3. Biomarker 2; d) tDCS output at high current Task or instruction set 4. Biomarker 3; e) No electromagnetic output. Instruction set 5.

Still referring to FIG. 7, the biomarkers can access at least one aspect of nervous system function. In the sequence above a preferred biomarker is heart rate variability. In the sequence above a preferred biomarker is impedance. In the sequence above a preferred biomarker is transimpedance. The aforementioned sequence can also be applied to generate high frequency tACS. In such cases each instance of not high current tDCS above is replaced with tACS that is not high frequency, and each instance of high current tDCS is replaced with tACS that is high frequency. The sequence above can be applied with bilateral electrode placement across all states. The sequences above can include a change in electrode placement. In one embodiment high frequency tACS is combined with tDCS. A 1-6 mA tDCS may be combined with 0.1-100 kHz tACS at 0.1-2 mA. In a preferred embodiment 2-4 mA tDCS is combined with 0.1-2 mA tACS at 1-50 kHz. The combined waveform is applied for 20 seconds to 60 minutes, preferable for 5-30 minutes. On one embodiment the frequency of the kHz tACS is increased proportionally to the tDCS intensity. The combination of tDCS and kHz tACS provides integrated benefit of both modalities when applied to closed-loop stimulation based on BTT.

In some embodiments of at least one aspect, the time course of energy administration is determined a priori as a cumulative multi-step treatment period.

In one embodiment, the EEG spectrum associated with preselected or target intrinsic frequency is set from 1.5 Hz to 150 Hz, where the pre-selected or target intrinsic frequency is greater than 1 Hz but less than 30 Hz, and may be phase locked to the EEG. In one embodiment, the EEG spectrum associated with preselected or target intrinsic frequency is set from 20 Hz to 100 Hz. In one embodiment, the EEG spectrum associated with preselected or target intrinsic frequency is set from 60 Hz to 70 Hz. In some embodiments, magnetic field is administered to the primary motor cortex and in addition a MEG be used.

In yet another embodiment, some aspects may deploy heart rate variability (heart rate variability) signal feedback monitor to either user or an operator. In one embodiment, there is a plurality of configurable wearable sensor and electrodes affixed in a packet to generate and sense electrical or optic signals based on electrical or emissivity properties of the patient's heart or other tissue compartments proximal and at the target location. In yet another embodiment, the heart rate variability signal is stored digitally for computing later in a memory or cloud by a cluster of computing processors. The configurable processor transmits initiation signal to the controller 110 that will control the stimulation signal to ensure whether the sensed heart rate variability matches the historically stored heart rate variability feedback criteria.

Still referring to FIG. 7, in one embodiment, the heart rate variability processing pipeline has the flexibility in storing heart rate variability data for later analysis, programming and controlling the stimulus (e.g., electrical, optical, magnetic, vibration) and displaying it in user interface through wired or wireless connection. In yet another embodiment, the heart rate variability signal is amplified using a high input impedance operational amplifier with zero output impedance, infinite open-loop gain, zero input offset voltage, infinite bandwidth with zero phase shift, and zero noise.

In one embodiment, at least one aspect of the BTT includes bioimpedance is measured by applying low frequency and intensity ac waveforms and measuring the change in potential between the electrodes. In one embodiment two electrodes are used to provide a test current and two separate electrodes are use as bioimpedance sensors. In one embodiment two electrodes are used to provide a test current and three separate electrodes are use as bioimpedance sensors. In one embodiment two electrodes are used to provide a test current and four separate electrodes are use as bioimpedance sensors. In yet another embodiment, the artifact in the bioimpedance signal is canceled using a high pass filter, correlation filter, or an artifact model, all incorporated in the processor that collects the sensed signal.

In some embodiments, the affixed packet has a configurable tactile or vibration device that when activated transmit a perceptible vibration signal pulsing at 1 Hz to 5 kHz, preferably at 1 Hz-120 Hz to the user.

The BTT control software and methods can provide diagnostics as well as engagement component therapeutics. The analysis of subject BTT against BTT templates allows personalized medicine systems. The engagement component inclusion of questions and analysis of answers with associated feature importance against BTT templates assess brain function and allow a subject to be diagnosed with fewer questions, and that BTT based diagnosis can be repeated regularly, for example at each engagement to support frequency energy application and state block adjustments thereby improving therapy benefit and decreasing possible side effects.

Figure 8:
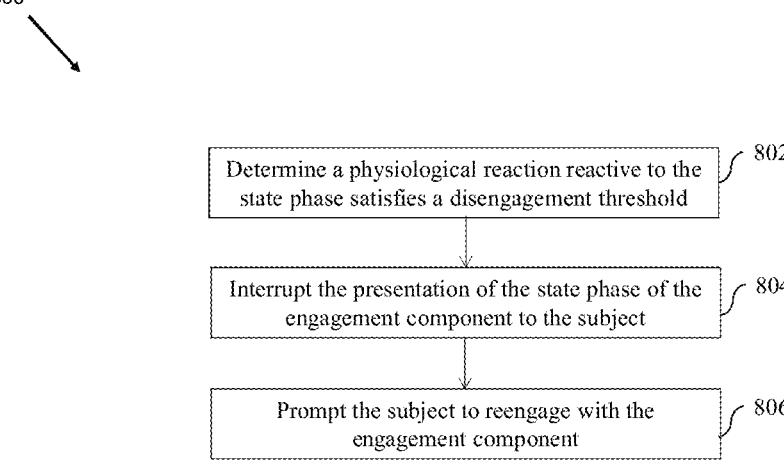
FIG. 8 depicts an example of a flowchart of a method configured to interrupt the presentation of the state phase of the engagement component to the subject in response to a physiological reaction reactive to the state phases satisfying a disengagement threshold.

Referring now to FIG. 8, illustrated is a flowchart of a method configured to interrupt the presentation of the state phase of the engagement component to the subject in response to a physiological reaction reactive to the state phases 114 satisfying a disengagement threshold. The reengagement flowchart 800 may interrupt the presentation of the state phase 114 to prompt the subject to reengage with the engagement component. At 802, the controller 110 may determine a physiological reaction reactive to the state phase satisfies a disengagement threshold. For example, the controller 110 may determine that physiological reaction of the subject does not match an expected physiological reaction. At 804, the controller 110 may interrupt the presentation of the state phase of the engagement component to the subject. At 806, the controller 110 may prompt the subject to reengage with the engagement component. In some embodiments, the controller 110 may determine that a new engagement component is to be presented based on the subject inability to remain attentive the cues, prompts, or otherwise unresponsive to the phase state. The controller 110 may select the new engagement component physiological reaction of the subject based on satisfying a disengagement threshold and the determined severity of the disengagement.

A physiological wellness control system 100 may be used to treat attention disorders. The engagement component may be configured to engage the brain in a manner that depends on attention. The controller 110 may determine the physiological reaction reactive to the state phase satisfies the disengagement threshold. The disengagement threshold may be indicative of the subject failing to engage with the engagement component. Performance may be accessed with an interactive task and prompts. Attention may be measured by EEG as a physiological marker. Attention may be measured by ECG physiological markers. Attention may be measured by transimpedance. The physiological maker will be time dependent depending on the state-phase block. For example, there may be a low-engagement state phase block during which time the attention related activity of the physiological marker should be relatively low followed by high-engagement state phase block during which time the attention related activity of the physiological marker should be relatively high. The transition from low to high state will depend on the nature of the state phase block and the subject state. Hence the BTT is sensitive to subject state.

Energy application alters the BTT with the goal of adjusting subject state. The control system can adjust the energy based on the detected BTT compared to a desired BTT. The control system can adjust the state phase block to accommodate for subject performance, adjust the BTT, or optimize detection of the BTT. If a subject is showing no change in physiological marker between the low engagement and the high engagement phase, the state phase blocks are adjusted to increase change in physiological marker between the low engagement and the high engagement phase. The difficulty of tasks can be increased if subject performance is high. The difficulty of tasks can be decreased if subject performance is high. The controller 110 may interrupt the presentation of the state phase of the engagement component to the subject in response to the physiological reaction reactive to the state phase satisfying the disengagement threshold. The controller 110 may prompt the subject to reengage with the engagement component in response to the physiological reaction reactive to the state phase satisfying the disengagement threshold.

Still referring to FIG. 8, the physiological wellness control system 100 may be used to treat cognitive fatigue. The engagement component includes a cognitive training task which involves a sequence of sub-tasks in the state phase. The engagement component is approximately 30 minutes with 6-five minute state phases 114. The task performance depends on attention to tasks in each state phase. Lack of attention or poor attention may result in a decrease in performance. The physiological wellness control system 100 monitors task performance. The control system monitors physiological state of the subject. The projected BTT for an ideal or target subject is predicted over time given the engagement component by the physiological wellness control system 100 or other system. The task performance and physiological measures determined by the physiological wellness control system 100 or other system are used to calculate the actual BTT. Stimulation from the energy application system 130 is applied if the actual BTT is sufficiently different from the target BTT. Changes in resulting performance and physiological measurements are then re-accessed in the context of the current state phase.

Figure 9:
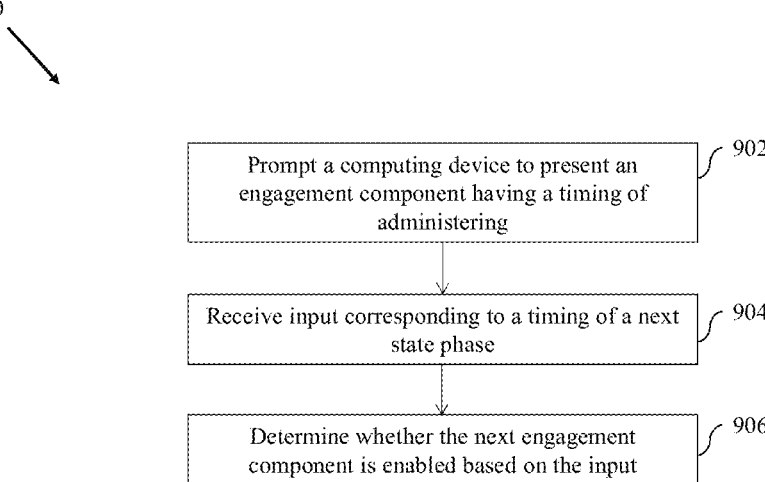
FIG. 9 depicts an example of a flowchart of a method configured to determine whether the next engagement component is enabled based on an input.

Referring to FIG. 9, illustrated is a flowchart of a method configured to determine whether the next engagement component is enabled based on an input. The next engagement component flowchart 900 may determine whether the next engagement component is enabled based on user input. At step 902, the controller 110 may prompt a computing device 120 to present an engagement component having a timing of administering. At step 904, the controller may receive input corresponding to a timing of a next state phase. At step 906, the controller may determine whether the next engagement component is enabled based on the component.

The processor unit may be programmed with instructions that based on the current BTT and BTT database may modify the state phase of the engagement component in response to received input from the subject, including displaying an updated task of the state phase to the subject. The sequence of engagement components 112 may include the timing of administering a next electromagnetic dose in response to the BTT analyzed from the subject performance. The input from the subject forming the BTT may comprise answers to one or more questions during the state phase or after the state phase. The processor unit may be programmed with instructions to prompt the subject indicating instruction for the task of the next state phase or the timing of a break until the next state phase when the state phase is the last of an engagement component. The processor unit may be programmed with instructions to prompt the operator to enter a code, such as a completion code. The processor unit may be programmed with instructions to prompt the operator to enter a code, such as an activation code.

The activation code is linked to a specific state phase or sequence of state phases 114 that are then provided. A look-up table may relate the activation code with the specific state phase to be applied. The look-up table may be device specific and reprogrammed at each instance of a new subject. The processor unit may be programmed to automatically unlock device administering electromagnetic dose based on set intervals (for instance, one session per day in tDCS). This option avoids the need to enter any activation code but similar to above, a look-up table may relate the session (as unique timestamp is logged) to the specific state phase to be applied.

Still referring to FIG. 9, the processor unit may be programmed with instructions to display a score result of a specific state phase task, or of the aggregate performance in the engagement components 112. The processor unit may be programmed with instructions to provide or more questions related to the subjects used of a pharmacologic agent. The processor unit may be programmed with instructions to provide or more questions related to the sensations experienced by the subject during the engagement component. Such a questionnaire may be a visual analog scale (VAS) or pain.

BTT of the subject can be estimated based on demographic data and measured biomarkers in order to determine an improved state phase or engagement component.

BTT may include data from answers to a plurality of questions related to cognitive function of the patient or data aggregated from a task. Data for the patient population may comprise answers to the same plurality of questions related to cognitive functions of the patient population members. The engagement component may comprise the timing and waveform of the electromagnetic dose. The state phases 114 of the engagement modulate may be configured to determine the individual therapeutic treatment plan in response to the data for the subject. This generates individual BTT trajectories.

Still referring to FIG. 9, the programmed therapeutic module can employ a therapy classifier, for example an artificial intelligence classifier, an signal processing classifier, or a statistical modeling classifier, or a machine learning classifier to determine the optimal state phase. An engagement component or engagement component sequence may comprise a customized individualized sequence or selected of phase sets The sequence may be individualized to treat deficits of brain functions such as cognitive function. The systems and methods disclosed herein are capable of providing improved state phase selection from the set for optimized therapy. This optimized therapy can include selection of stimulation modality or task. Improved dosing of a stimulation may be implemented by a programmed therapeutic module that can select the optimal state phase. The classier leverages information provided from prompts provided to subjects in designated prior state phases. Questions can assess cognitive performance. Questions may be accessed using a website or a mobile device. Cognitive performance may be accessed by performance on the task in the state phase. The mobile device can be programmed at least one question and receive a plurality of answers, and display the information for the next state phase to the user. The questions and tasks were provided to the training population in the first stage to develop normative BTT.

In an aspect, a digital therapeutic system with an electric waveform generator to treat a subject with an individual therapeutic treatment plan consisting of at least one engagement component may comprise a processor comprising programmed instructions for: 1) a diagnostic module to receive input for the patient and output diagnostic data for the patient; and 2) a therapeutic module including digital therapy and an electric waveform generator controller to receive the diagnostic data for the patient and output the individual therapeutic treatment plan for the patient. The controller 110 may comprise a classifier selected from the group consisting of a signal processing, linear regression. machine learning classifier, an artificial intelligence classifier, and a statistics model classifier. The diagnostic classifier may be based on data for pre-assessed larger subject populations to guide the classification of the diagnostic data for the patient. The therapeutic treatment including at least one engagement component plan may comprise timing or an amount of an electromagnetic dose. The therapeutic classifier may comprise a therapy classifier selected from the group consisting of signal processing, linear regression, machine learning classifier, an artificial intelligence, and a statistics model classifier. The therapeutic classifier programming may be based on the data collected beforehand on selected subject populations to determine the timing or amount of the electromagnetic dose for the subject.

The individual therapy can include at least two stages. The first stage involves the therapy provider making decision. The second stage involves the automatic device making decisions through the programming described based on the ongoing BTT. At least some of the shortcomings of the prior methods may be overcome through this two stage implementation. In one embodiment the operator chooses from at least two treatment modes. A treatment mode consists of potential engagement components 112 and state phases 114, along with a program to adjust state phases 114 and select engagement components 112 based on BTT, and possible energy application modes that are part of the state phases 114. Two subjects may be assigned different treatment modes based on various diagnostic decisions made by the operator. For example one mode will be selected for a subject demonstrating atypical anxiety and will include galvanic skin monitoring based biomarker and tDCS electric waveform generator (EWG). For example one more will be selected for a subject demonstrating atypical mood and will include guided meditation, tDCS EWG, and heart rate variability based biomarker.

Still referring to FIG. 9, the individual personal treatment plan can be based at least in part on answers provided by the subject to a prescribed set of one or more questions that serve to parametrize a BTT trajectory. The questionnaires can be provided by a mobile device. The questionnaire can be replaced by cognitive assessment. From a set of possible BTT trajectories the questions allow selection on one or a sub-set of likely BTT trajectories. The operator may select an initial therapy plan (the first stage) informed by this projection. A therapeutic treatment plan provided in two stages based on the BTT methods and systems as described herein addresses at least some of the shortcomings of prior methods and systems by improving the precision of the individual therapy.

The intensity of electromagnetic stimulation can be a function of the deviation of the current BTT from the desired BTT. The intensity of electromagnetic stimulation can be a function of the deviation of the projected BTT from the desired projected BTT. In one embodiment the intensity of tDCS is a linear function of the error. In a further embodiment the intensity of tDCS is a linear function of the error bounded by a minimum tDCS intensity and maximum tDCS intensity. The minimum tDCS intensity may be 0.1 or 0.5 or 1 mA. The maximum tDCS intensity may be 2 mA, or 3 mA, or 5 mA, or 6 mA. High intensity tDCS may be the upper bound as described. The bounding may change from one state phase to another state phase. In one embodiment the maximum tDCS current bounding is 2 mA and in a later state page the maximum tDCS current bounding is 4 mA or 6 mA. The transition of maximum tDCS bounding can be guided by answers provided by the subject or biomarkers. In a preferred embodiment these biomarkers are heart rate variability or transimpedance.

Figure 10:
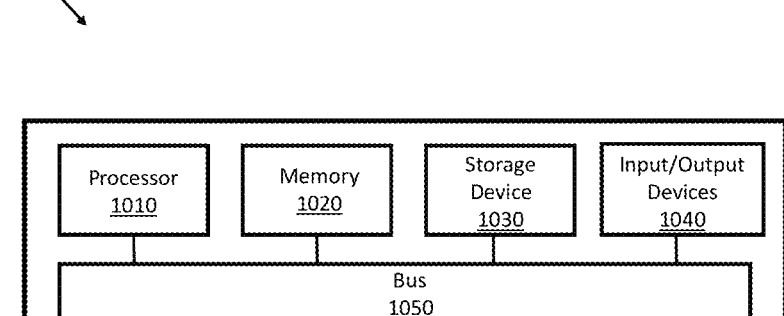
FIG. 10 depicts a block diagram illustrating a computing system consistent with implementations of the current subject matter.

Referring to FIG. 10, the computing system 1000 may include a processor 1010, a memory 1020, a storage device 1030, and an input/output device 1040. The processor 1010, the memory 1020, the storage device 1030, and the input/output device 1040 may be interconnected via a system bus 1050. The processor 1010 is capable of processing instructions for execution within the computing system 1000. Such executed instructions may implement one or more components of, for example, hardware for controlling the physiological state. In some exemplary embodiments, the processor 1010 may be a single-threaded processor. Alternately, the processor 1010 may be a multi-threaded processor. The processor 1010 is capable of processing instructions stored in the memory 1020 and/or on the storage device 1030 to display graphical information for a user interface provided via the input/output device 1040.

The memory 1020 is a non-transitory computer-readable medium that stores information within the computing system 1000. The memory 1020 may be configured to store data structures representing configuration object databases, for example. The storage device 1030 is capable of providing persistent storage for the computing system 1000. The storage device 1030 may be a floppy disk device, a hard disk device, an optical disk device, or a tape device, or other suitable persistent storage means. The input/output device 1040 provides input/output operations for the computing system 1000. In some exemplary embodiments, the input/output device 1040 includes a keyboard and/or pointing device. In various implementations, the input/output device 1040 includes a display unit for displaying graphical user interfaces.

According to some exemplary embodiments, the input/output device 1040 may provide input/output operations for a network device. For example, the input/output device 1040 may include Ethernet ports or other networking ports to communicate with one or more wired and/or wireless networks (e.g., a local area network (LAN), a wide area network (WAN), the Internet, a public land mobile network (PLMN), and/or the like).

In some exemplary embodiments, the computing system 1000 may be used to execute various interactive computer software applications that may be used for organization, analysis, and/or storage of data in various formats. Alternatively, the computing system 1000 may be used to execute any type of software applications. These applications may be used to perform various functionalities, e.g., planning functionalities (e.g., generating, managing, editing of spreadsheet documents, word processing documents, and/or any other objects, etc.), computing functionalities, communications functionalities, etc. The applications may include various add-in functionalities or may be standalone computing items and/or functionalities. Upon activation within the applications, the functionalities may be used to generate the user interface provided via the input/output device 1040. The user interface may be generated and presented to a user by the computing system 1000 (e.g., on a computer screen monitor, etc.).

Figures 11A, 11B, 11C:
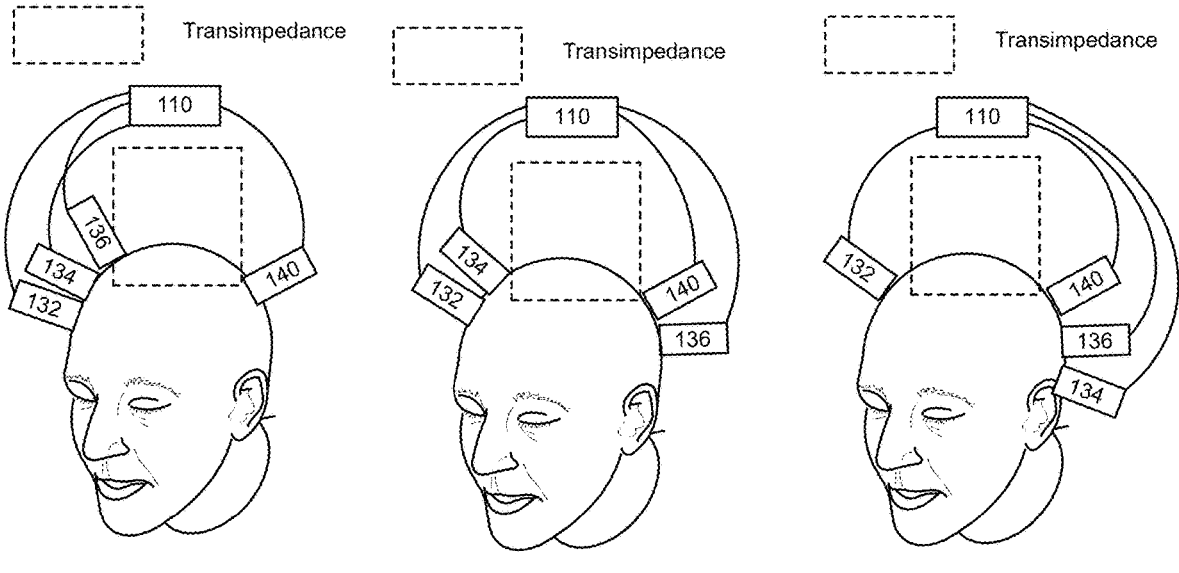
FIG. 11A depicts a transimpedance zone measured and/or created by the physiological wellness control system connected to the head of the human patient via a pair of electrical cables with three energy-emitting devices and a sensor at their respective distal ends.
FIG. 11B depicts a transimpedance zone measured by and/or created by the physiological wellness control system where the physiological wellness control system is connected to the head of the human patient via a pair of electrical cables with three energy-emitting devices and a sensor at their respective distal ends.
FIG. 11C depicts a transimpedance zone measured by and/or created by the physiological wellness control system where the physiological wellness control system is connected to the head of the human patient via a pair of electrical cables with three energy-emitting devices and a sensor at their respective distal ends.

FIG. 11A depicts a transimpedance zone measured and/or created by the physiological wellness control system 100 connected to the head of the human patient via a pair of electrical cables with three energy-emitting devices 132, 134, 136 and the sensor 140 at their respective distal ends. The energy-emitting devices 132, 134, 136 may be positioned near a proximate side of the top of the patient's head and the sensor 140 may be positioned at a distal end at the top of the patient's head. The sensor 140 may be positioned at least several centimeters away from the energy-emitting devices 132, 134, 136. The transimpedance zone may be formed between the energy-emitting devices 132, 134, 136 and the sensor 140.

FIG. 11B depicts a transimpedance zone measured by and/or created by the physiological wellness control system 100 where the physiological wellness control system 100 is connected to the head of the human patient via a pair of electrical cables with three energy-emitting devices 132, 134 and a sensor 140 at their respective distal ends. The energy-emitting devices 132, 134 may be positioned near a proximate side of the top of the patient's head and the sensor 140 and the energy-emitting device 136 may be positioned at a distal end at the top of the patient's head. The sensor 140 and the energy-emitting device 136 may be positioned at least several centimeters away from the energy-emitting devices 132, 134. The transimpedance zone may be formed between the energy-emitting devices 132, 134 and the sensor 140 next to the energy-emitting device 136.

FIG. 11C depicts a transimpedance zone measured by and/or created by the physiological wellness control system 100 where the physiological wellness control system 100 is connected to the head of the human patient via a pair of electrical cables with three energy-emitting devices 132, 134, 136 and a sensor 140 at their respective distal ends. The energy-emitting device 132 may be positioned near a proximate side of the top of the patient's head and the sensor 140 and the energy-emitting devices 134, 136 may be positioned at a distal end at the top of the patient's head. The sensor 140 and the energy-emitting devices 134, 136 may be positioned at least several centimeters away from the energy-emitting device 132. The transimpedance zone may be formed between the energy-emitting device 132 and the sensor 140 next to the energy-emitting devices 134, 136.

Figure 11D:
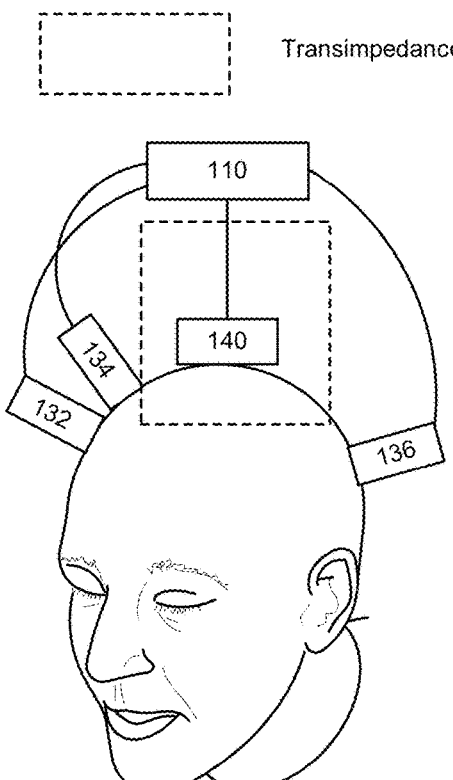
FIG. 11D depicts a transimpedance zone measured by and/or created by the physiological wellness control system connected to the head of the human patient via a pair of electrical cables with three energy-emitting devices and a sensor at their respective distal ends.

FIG. 11D depicts a transimpedance zone measured by and/or created by the physiological wellness control system 100 connected to the head of the human patient via a pair of electrical cables with three energy-emitting devices 132, 134, 136 and a sensor 140 at their respective distal ends. The energy-emitting devices 132, 134 may be positioned near a proximate side of the top of the patient's head and the energy-emitting device 136 may be positioned at a distal end at the top of the patient's head. The energy-emitting device 136 may be positioned at least several centimeters away from the energy-emitting devices 132, 134. The transimpedance zone may be formed between the energy-emitting devices 132, 134 and the energy-emitting device 136. The sensor 140 may be positioned in the transimpedance zone between the energy-emitting devices 132, 134 and the energy-emitting device 136.

Figure 11E:
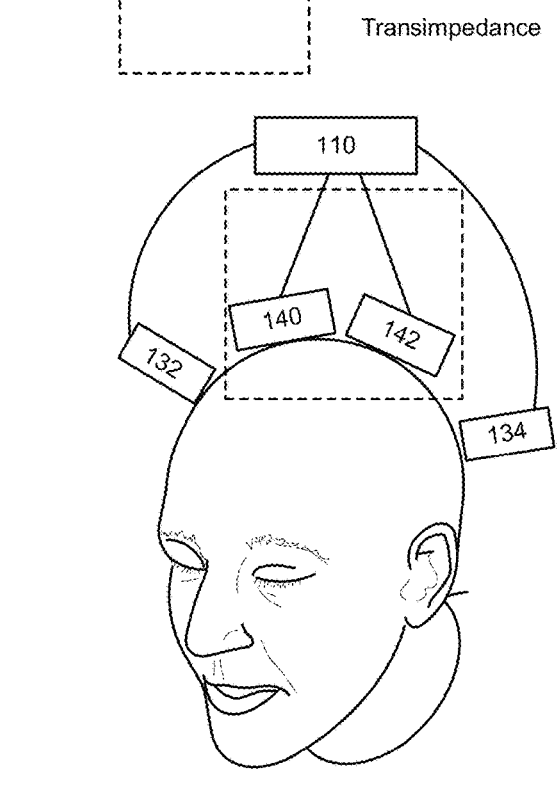
FIG. 11E depicts a transimpedance zone measured by and/or created by the physiological wellness control system where the physiological wellness control system is connected to the head of the human patient via a pair of electrical cables with two energy-emitting devices and two sensors at their respective distal ends.

FIG. 11E depicts a transimpedance zone measured by and/or created by the physiological wellness control system 100 where the physiological wellness control system 100 is connected to the head of the human patient via a pair of electrical cables with two energy-emitting devices 132, 134 and two sensors 140, 142 at their respective distal ends. The energy-emitting device 132 may be positioned near a proximate side of the top of the patient's head and the energy-emitting device 134 may be positioned at a distal end at the top of the patient's head. The energy-emitting device 134 may be positioned at least several centimeters away from the energy-emitting device 132. The transimpedance zone may be formed between the energy-emitting device 132 and the energy-emitting device 134. The sensors 140, 142 may be positioned in the transimpedance zone between the energy-emitting device 132 and the energy-emitting device 136.

FIG. 11F depicts a computing device connected to receive input from the hand of the human patient and three energy-emitting devices and a sensor connected to the head of the human patient. The energy-emitting devices 132, 134, 136 may be positioned near a proximate side of the top of the patient's head and the sensor 140 may be positioned at a distal end at the top of the patient's head. The sensor 140 may be positioned at least several centimeters away from the energy-emitting devices 132, 134, 136. The energy-emitting devices 132, 134, 136 may generate signals in response to input from the computing device 120. The sensor 140 may be configured to detect signals in response to input from the computing device 120. The computing device 120 may include a user interface 125 configured to receive user input.

FIG. 11G depicts a computing device 120 connected to receive input from the hand of the human patient, a sensor 140 connected at the hand, and two energy-emitting devices 132, 134 connected to the head of the human patient. The energy-emitting devices 132, 134 may be positioned near a proximate side of the top of the patient's head and the sensor

140 may be positioned at a computing device proximate to the user hand. The energy-emitting devices 132, 134 may generate signals in response to input from the computing device 120. The sensor 140 may be configured to detect signals in response to input from the computing device 120. The computing device 120 may include a user interface 125 configured to receive user input.

FIG. 11H depicts a computing device 120 connected to receive input from the hand of the human patient, two sensors 140, 142 connected at the hand, and two energy-emitting devices 132, 134 connected to the head of the human patient. The energy-emitting devices 132, 134 may be positioned near a proximate side of the top of the patient's head and the sensors 140, 142 may be positioned at a computing device proximate to the user hand. The energy-emitting devices 132, 134 may generate signals in response to input from the computing device 120. The sensor 140 may be configured to detect signals in response to input from the computing device 120. The computing device 120 may include a user interface 125 configured to receive user input.

Figures 11I, 11J:
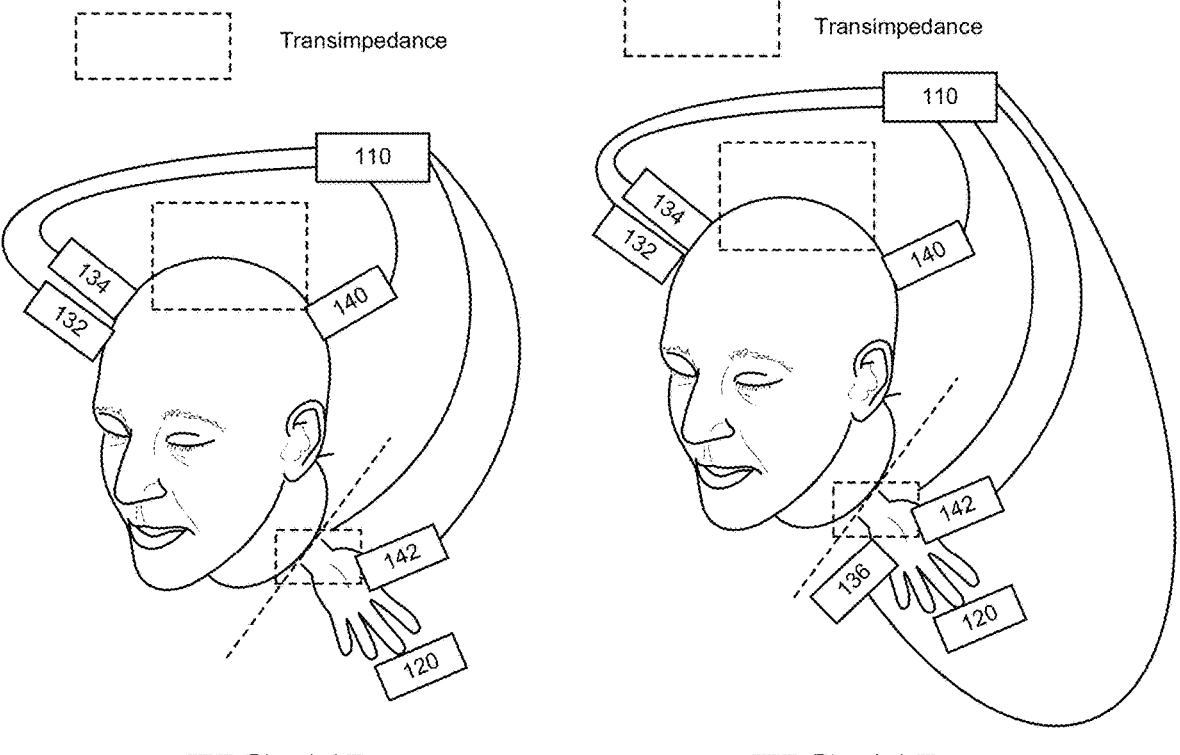
FIG. 11I depicts two transimpedance zones measured by and/or created by the physiological wellness control system with a first transimpedance zone at the hand of the human patient and a second transimpedance zone at the head of the human patient.
FIG. 11J depicts two transimpedance zones measured by and/or created by the physiological wellness control system with a first transimpedance zone at the hand of the human patient and a second transimpedance zone at the head of the human patient.

FIG. 11I depicts two transimpedance zones measured by and/or created by the physiological wellness control system with a first transimpedance zone at the hand of the human patient and a second transimpedance zone at the head of the human patient. The energy-emitting devices 132, 134 may be positioned near a proximate side of the top of the patient's head and the sensor 140 may be positioned at a distal end at the top of the patient's head. The second transimpedance zone may be formed between the energy-emitting devices 132, 134 and the sensor 140. The first transimpedance zone may be proximate to the hand of the human patient and may be proximate to the sensor 142 positioned at the hand of the human patient. The energy-emitting devices 132, 134 may generate signals in response to input from the computing device 120. The sensors 140, 142 may be configured to detect signals in response to input from the computing device 120. The computing device 120 may include a user interface 125 configured to receive user input.

FIG. 11J depicts two transimpedance zones measured by and/or created by the physiological wellness control system with a first transimpedance zone at the hand of the human patient and a second transimpedance zone at the head of the human patient. The energy-emitting devices 132, 134 may be positioned near a proximate side of the top of the patient's head and the sensor 140 may be positioned at a distal end at the top of the patient's head. The second transimpedance zone may be formed between the energy-emitting devices 132, 134 and the sensor 140. The first transimpedance zone may be proximate to the hand of the human patient and may be proximate to the sensor 142 and the energy emitting device 136 positioned at the hand of the human patient. The energy-emitting devices 132, 134, 136 may generate signals in response to input from the computing device 120. The sensors 140, 142 may be configured to detect signals in response to input from the computing device 120. The computing device 120 may include a user interface 125 configured to receive user input.

The terminology used herein is for the purpose of describing particular embodiments only and is not intended to be limiting of the embodiments. As used herein, the singular forms "a", "an" and "the" are intended to include the plural forms as well, unless the context clearly indicates otherwise. It will be further understood that the terms "comprises" and/or "comprising." when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" may be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

While the foregoing is directed to implementations of the present disclosure, other and further implementations of the disclosure may be devised without departing from the basic scope thereof, and the scope thereof is determined by the claims that follow.

What is claimed is:

1. A system comprising:

an energy application system configured to apply an electrical stimulation to a subject head of a subject for inducing a physiological reaction in the subject, the energy application system having at least a first energy-emitting device and a second energy-emitting device that support directionality of the electrical stimulation across the subject head;

a user device having a user interface, the user device configured to present cues to the subject via the user interface;

a sensor configured to couple to the subject to detect at least one feature of the physiological reaction of the subject; and a controller communicatively coupled to the energy application system, the user device, and the sensor, the controller configured for:

selecting a state phase based on an engagement component, the engagement component having a set of state phases and determinative of the state phase from the set of state phases, the set of state phases corresponding to at least one of the cues for presentation to the subject or electrical stimulations applied by the energy application system, the state phases configured to induce a set of physiological reactions from the subject measurable by the sensor;

prompting the user device to present a cue to the subject or the energy application system to apply the electrical stimulation to the subject based on the selected state phase;

measuring, in response to prompting the user device to present the cue to the subject or the energy application system to apply the electrical stimulation to the subject based on the selected state phase, the set of physiological reactions of the subject using the sensor, the set of physiological reactions induced by the selected state phase;

determining a subject bio-psychiatric therapeutic trajectory based on the measured set of physiological reactions from the subject, the subject bio-psychiatric therapeutic trajectory generated by mapping the set of physiological reactions from the subject to the state phase, the subject bio-psychiatric therapeutic trajectory being indicative of a physiological state pattern or a cognitive state of the subject;

determining, based on comparing the subject bio-psychiatric therapeutic trajectory to a plurality of historical bio-psychiatric therapeutic trajectories, a likelihood of at least one aspect of the physiological state pattern, the cognitive state, a mood, or a disease in the subject corresponds to at least one of an aspect-related bio-psychiatric therapeutic trajectory or a disease-related bio-psychiatric therapeutic trajectory from the plurality of historical bio-psychiatric therapeutic trajectories, the physiological state pattern, the cognitive state, the mood, or the disease in the subject matching at least one physiological pattern of the aspect-related bio-psychiatric therapeutic trajectory or the disease-related bio-psychiatric therapeutic trajectory;

selecting, in response to determining the likelihood of at least one of the physiological state pattern, the cognitive state, the mood, or the disease in the subject, an updated state phase to be presented to the subject to influence the subject bio-psychiatric therapeutic trajectory to match a healthy bio-psychiatric therapeutic trajectory, the updated state phase including at least one of an updated cue, an updated biofeedback, or an updated waveform from the energy application system applied to the subject head;

measuring a set of stimulation-induced physiological reactions from the subject using the sensor in response to prompting the user device to present the updated cue, the user device to present the updated biofeedback, or the energy application system to apply the updated waveform based on the updated state phase determining a modified subject bio-psychiatric therapeutic trajectory based on the stimulation-induced physiological reactions from the subject;

determining the modified subject bio-psychiatric therapeutic trajectory does not match the healthy bio-psychiatric therapeutic trajectory; and adjusting, in response to determining the modified subject bio-psychiatric therapeutic trajectory does not match the healthy bio-psychiatric therapeutic trajectory, the updated state phase to make the subject bio-psychiatric therapeutic trajectory match the healthy bio-psychiatric therapeutic trajectory by adjusting the electrical stimulation to the subject head, wherein at least one of an intensity, a pulse width, a time applied, or a frequency of the adjusted electrical stimulation is different from the electrical stimulation.

2. The system of claim 1, wherein the set of physiological reactions are at least one of a heart rate spectrum second-order metrics biomarker or a transimpedance biomarker, and wherein at least one physiological reaction of the set of physiological reactions is modulated by the energy application system coupled to the subject.

3. The system of claim 1, wherein the first energy-emitting device and the second energy-emitting device are electrodes, and wherein the sensor is configured to measure at least one of a DC component of a transimpedance measurement or an AC component of the transimpedance measurement representative of the physiological reaction, and wherein the sensor is configured to measure the transimpedance across at least the first energy-emitting device and the second energy-emitting device coupled to the subject head, the transimpedance representative of a coupling between the energy application system and an electro-impedance of the subject.

4. The system of claim 1, the controller further configured for:

calculating, in response to the state phase having a duration greater than 100 seconds and including at least 10 synchronized audio or visual cues, a rate of change of the physiological reaction in the subject;

calculating a difference between the rate of change of the physiological reaction in the subject and a rate of change of the physiological reaction in a set of healthy subjects responding to the state phase having the duration greater than 100 seconds and including at least the 10 synchronized audio or visual cues; and prompting, in response the difference between the rate of change of the physiological reaction in the subject and the rate of change of the physiological reaction in the set of healthy subjects satisfying a difference threshold, the energy application system to update an electrical feature of the electrical stimulation applied to the subject.

5. The system of claim 1, the controller further configured for:

calculating, in response to the state phase having a duration greater than 220 seconds and including at least 12 synchronized audio or visual cues, a rate of change of the physiological reaction in the subject;

calculating a difference between the rate of change of the physiological reaction in the subject and a rate of change of the physiological reaction in the set of healthy subjects responding to the state phase having the duration greater than 220 seconds and including at least the 12 synchronized audio or visual cues; and prompting, in response the difference between the rate of change of the physiological reaction in the subject and the rate of change of the physiological reaction in the set of healthy subjects satisfying a difference threshold, the energy application system to update an electrical feature of the electrical stimulation applied to the subject.

6. The system of claim 1, wherein the subject bio-psychiatric therapeutic trajectory is based on a subject mental state, a subject cognitive ability, a subject level of engagement with the engagement component, the engagement component, and the energy application system.

7. The system of claim 1, wherein the controller is further configured for:

determining, in response to presenting the state phase to the subject, whether the physiological reaction reactive to the state phase satisfies a non-normative threshold, the non-normative threshold being indicative of an expected physiological reaction of subjects reacting to the state phase based on the plurality of historical bio-psychiatric therapeutic trajectories; and selecting, in response to the physiological reaction reactive to the state phase satisfying the non-normative threshold, a new state phase from the set of state phases of the engagement component, the new state phase not predetermined to be presented as a next state phase after the state phase, and prompting the user device to present a new cue, the user device to present a new biofeedback, or the energy application system to apply a new waveform based on the new state phase.

8. The system of claim 7, wherein the controller is further configured for:

prompting, in response to the physiological reaction reactive to the state phase satisfying the non-normative threshold, the energy application system to apply the electrical stimulation with a modality of at least one of a tDCS, tACS, TMS, or tFUS current to the subject head, the at least one of tDCS, tACS, TMS, or tFUS current proven to adjust at least one of heart rate spectrum second-order metrics or a transimpedance across the first energy-emitting device and the second energy-emitting device coupled to the subject head.

9. The system of claim 8, wherein the controller is further configured for:

measuring, in response to prompting the energy application system to apply the electrical stimulation to the subject head, an unsatisfying physiological reaction from the subject using the sensor, the unsatisfying physiological reaction being induced by the energy application system coupled to the subject head, the unsatisfying physiological reaction failing to satisfy a healthy physiological reaction threshold indicative of a healthy physiological reaction by a healthy individual; and prompting, in response to measuring the unsatisfying physiological reaction from the subject using the sensor, the energy application system to apply a second electrical stimulation from the energy application system at the next state phase in the set of state phases of the engagement component, the second electrical stimulation to the subject head, the second electrical stimulation having a different modality from the at least one of tDCS, tACS, TMS, or tFUS current.

10. The system of claim 1, wherein the controller is further configured for:

determining the physiological reaction reactive to the state phase satisfies a disengagement threshold, the disengagement threshold being indicative of the subject failing to engage with the engagement component;

interrupting, in response to the physiological reaction reactive to the state phase satisfying the disengagement threshold, the presentation of the state phase of the engagement component to the subject; and prompting, in response to the physiological reaction reactive to the state phase satisfying the disengagement threshold, the subject to reengage with the engagement component.

11. The system of claim 1, wherein the cues corresponding to the state phase are updated at a peak rate between 20 Hz and 220 Hz, with at least one period where the state phase is not updated lasting greater than 1 second, and wherein an output of the energy application system updates at a rate 0.1 to 18 times the peak rate.

12. The system of claim 1, wherein the cues corresponding to the state phase are updated at a cue update rate between 0.001 Hz and 1 Hz, wherein the state phase has at least one period that is not updated lasting greater than 10 seconds, and wherein output of the energy application system updates at a rate 0.1 to 18 times the cue update rate.

13. The system of claim 1, wherein the engagement component includes at least one of a guided meditation, music, or a task, wherein the engagement component is configured to dynamically determine the state phase from the set of state phases based on subject attention to a previous state phase, and wherein each state phase of the set of state phases may be divided into multiple state phases to provide a new set of instructions to invoke a different physiological response corresponding to a change in the plurality of historical bio-psychiatric therapeutic trajectories, the new set of instructions related to the engagement component and that is selected based on subject attention.

14. The system of claim 1, wherein the energy application system is configured to generate a DC component feature and an AC component feature, and wherein the sensor is at least one of the first energy-emitting device and the second energy-emitting device coupled to the subject head.

15. A method comprising:

selecting a state phase based on an engagement component, the engagement component having a set of state phases and determinative of the state phase from the set of state phases, the set of state phases corresponding to a cue for presentation to a subject or electrical stimulations applied by an energy application system, the energy application system configured to apply an electrical stimulation to a subject head of the subject for inducing a physiological reaction in the subject, the energy application system having at least a first energy-emitting device and a second energy-emitting device that support directionality of the electrical stimulation across the subject head, the state phases configured to induce a set of physiological reactions from the subject measurable by a sensor, the sensor configured to couple to the subject to detect at least one feature of the physiological reaction of the subject;

prompting a user device to present the cue to the subject or the energy application system to apply the electrical stimulation to the subject based on the selected state phase, the user device having a user interface, the user device configured to present cues to the subject via the user interface;

measuring, in response to prompting the user device to present the cue to the subject or the energy application system to apply the electrical stimulation to the subject based on the selected state phase, the set of physiological reactions of the subject using the sensor, the set of physiological reactions induced by the selected state phase;

determining a subject bio-psychiatric therapeutic trajectory based on the measured set of physiological reactions from the subject, the subject bio-psychiatric therapeutic trajectory generated by mapping the set of physiological reactions from the subject to the state phase, the subject bio-psychiatric therapeutic trajectory being indicative of a physiological state pattern or a cognitive state of the subject;

determining, based on comparing the subject bio-psychiatric therapeutic trajectory to a plurality of historical bio-psychiatric therapeutic trajectories, a likelihood of at least one aspect of the physiological state pattern, the cognitive state, a mood, or a disease in the subject corresponds to at least one of an aspect-related bio-psychiatric therapeutic trajectory or a disease-related bio-psychiatric therapeutic trajectory from the plurality of historical bio-psychiatric therapeutic trajectories, the physiological state pattern, the cognitive state, the mood, or the disease in the subject matching at least one physiological pattern of the aspect-related bio-psychiatric therapeutic trajectory or the disease-related bio-psychiatric therapeutic trajectory;

selecting, in response to determining the likelihood of at least one of the physiological state pattern, the cognitive state, the mood, or the disease in the subject, an updated state phase to be presented to the subject to influence the subject bio-psychiatric therapeutic trajectory to match a healthy bio-psychiatric therapeutic trajectory, the updated state phase including at least one of an updated cue, an updated biofeedback, or an updated waveform from the energy application system applied to the subject head;

measuring a set of stimulation-induced physiological reactions from the subject using the sensor in response to prompting the user device to present the updated cue, the user device to present the updated biofeedback, or the energy application system to apply the updated waveform based on the updated state phase determining a modified subject bio-psychiatric therapeutic trajectory based on the stimulation-induced physiological reactions from the subject;

determining the modified subject bio-psychiatric therapeutic trajectory does not match the healthy bio-psychiatric therapeutic trajectory; and adjusting, in response to determining the modified subject bio-psychiatric therapeutic trajectory does not match the healthy bio-psychiatric therapeutic trajectory, the updated state phase to make the subject bio-psychiatric therapeutic trajectory match the healthy bio-psychiatric therapeutic trajectory by adjusting the electrical stimulation to the subject head, wherein at least one of an intensity, a pulse width, a time applied, or a frequency of the adjusted electrical stimulation is different from the electrical stimulation.

16. The method of claim 15, wherein the set of physiological reactions are at least one of a heart rate spectrum second-order metrics biomarker or a transimpedance biomarker, and wherein at least one physiological reaction of the set of physiological reactions is modulated by the energy application system coupled to the subject.

17. The method of claim 16, wherein the first energy-emitting device and the second energy-emitting device are electrodes, and wherein the sensor is configured to measure at least one of a DC component of a transimpedance measurement or an AC component of the transimpedance measurement representative of the physiological reaction, and wherein the sensor is configured to measure the transimpedance across at least the first energy-emitting device and the second energy-emitting device coupled to the subject head, the transimpedance representative of a coupling between the energy application system and an electro-impedance of the subject.

18. A non-transitory computer-readable storage medium comprising at least one program for execution by one or more processors of a first device, the at least one program including instructions which, when executed by the one or more processors, cause the first device to perform operations comprising:

selecting a state phase based on an engagement component, the engagement component having a set of state phases and determinative of the state phase from the set of state phases, the set of state phases corresponding to a cue for presentation to a subject or electrical stimulations applied by an energy application system, the energy application system configured to apply an electrical stimulation to a subject head of the subject for inducing a physiological reaction in the subject, the energy application system having at least a first energy-emitting device and a second energy-emitting device that support directionality of the electrical stimulation across the subject head, the state phases configured to induce a set of physiological reactions from the subject measurable by a sensor, the sensor configured to couple to the subject to detect at least one feature of the physiological reaction of the subject;

prompting a user device to present the cue to the subject or the energy application system to apply the electrical stimulation to the subject based on the selected state phase, the user device having a user interface, the user device configured to present cues to the subject via the user interface;

measuring, in response to prompting at least one of the user device to present the cue to the subject or the energy application system to apply the electrical stimulation to the subject based on the selected state phase, the set of physiological reactions of the subject using the sensor, the set of physiological reactions induced by the selected state phase;

determining a subject bio-psychiatric therapeutic trajectory based on the measured set of physiological reactions from the subject, the subject bio-psychiatric therapeutic trajectory generated by mapping the set of physiological reactions from the subject to the state phase, the subject bio-psychiatric therapeutic trajectory being indicative of a physiological state pattern or a cognitive state of the subject;

determining, based on comparing the subject bio-psychiatric therapeutic trajectory to a plurality of historical bio-psychiatric therapeutic trajectories, a likelihood of at least one aspect of the physiological state pattern, the cognitive state, a mood, or a disease in the subject corresponds to at least one of an aspect-related bio-psychiatric therapeutic trajectory or a disease-related bio-psychiatric therapeutic trajectory from the plurality of historical bio-psychiatric therapeutic trajectories, the physiological state pattern, the cognitive state, the mood, or the disease in the subject matching at least one physiological pattern of the aspect-related bio-psychiatric therapeutic trajectory or the disease-related bio-psychiatric therapeutic trajectory;

selecting, in response to determining the likelihood of at least one of the physiological state pattern, the cognitive state, the mood, or the disease in the subject, an updated state phase to be presented to the subject to influence the subject bio-psychiatric therapeutic trajectory to match a healthy bio-psychiatric therapeutic trajectory, the updated state phase including at least one of an updated cue, an updated biofeedback, or an updated waveform from the energy application system applied to the subject head;

measuring a set of stimulation-induced physiological reactions from the subject using the sensor in response to prompting the user device to present the updated cue, the user device to present the updated biofeedback, or the energy application system to apply the updated waveform based on the updated state phase determining a modified subject bio-psychiatric therapeutic trajectory based on the stimulation-induced physiological reactions from the subject;

determining the modified subject bio-psychiatric therapeutic trajectory does not match the healthy bio-psychiatric therapeutic trajectory; and adjusting, in response to determining the modified subject bio-psychiatric therapeutic trajectory does not match the healthy bio-psychiatric therapeutic trajectory, the updated state phase to make the subject bio-psychiatric therapeutic trajectory match the healthy bio-psychiatric therapeutic trajectory by adjusting the electrical stimulation to the subject head, wherein at least one of an intensity, a pulse width, a time applied, or a frequency of the adjusted electrical stimulation is different from the electrical stimulation.

* * * * *